(12) United States Patent
Gary et al.

(10) Patent No.: US 7,084,163 B2
(45) Date of Patent: Aug. 1, 2006

(54) HETEROCYCLIC CARBOXAMIDES AND THEIR USE AS FUNGICIDES

(75) Inventors: Stéphanie Gary, Lyons (FR); Tim Lange, Lyons (FR); Benoît Muller, Lyons (FR); Christopher Richard Steele, Lyons (FR); Geoffrey Gower Briggs, Hertfordshire (GB); Joseph Perez, Lyons (FR); Alain Villier, Saint-Didier-au-Mont-d'Or (FR); Brian Hill, Lyons (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 10/483,518

(22) PCT Filed: Jul. 8, 2002

(86) PCT No.: PCT/EP02/08666

§ 371 (c)(1),
(2), (4) Date: Apr. 1, 2004

(87) PCT Pub. No.: WO03/006454

PCT Pub. Date: Jan. 23, 2003

(65) Prior Publication Data

US 2004/0152698 A1    Aug. 5, 2004

(30) Foreign Application Priority Data

Jul. 10, 2001   (EP) .................................. 01420154

(51) Int. Cl.
*A01N 43/80*     (2006.01)
*C07D 261/06*    (2006.01)
(52) U.S. Cl. ...................................... 514/378; 548/244
(58) Field of Classification Search ................ 548/244; 514/378
See application file for complete search history.

(56) References Cited

U.S. PATENT DOCUMENTS

| | | |
|---|---|---|
| 3,959,481 A | 5/1976 | Davis et al. |
| 4,001,416 A | 1/1977 | Pommer et al. |
| 4,054,585 A | 10/1977 | Felauer et al. |
| 4,214,090 A | 7/1980 | Huppatz |
| 5,223,526 A | 6/1993 | McLoughlin et al. |

FOREIGN PATENT DOCUMENTS

| | | |
|---|---|---|
| DE | 198 42 354 | 3/2000 |
| DE | 199 58 166 | 12/2000 |
| EP | 0 151 866 | 8/1985 |
| EP | 0 198 311 | 10/1986 |
| WO | WO 99/62915 | 12/1999 |
| WO | WO 01/49664 | 7/2001 |
| WO | WO 01/53259 | 7/2001 |

OTHER PUBLICATIONS

J.K. Sugden, et al.: "Anti-inflammatory activity of some N-substituted 3-carboxamido-4-hydroxy-5-oxo-3-pyrrolines".
European Journal of Medicinal Chemistry, vol. 14, No. 2, 1979, pp. 189-190, XP009003721 p. 190; table 1.
Z.D. Liu et al.: "Synthesis of 2-Amido-3-hydroxypridin-4(1H)-ones. Novel Iron Chelators with Enhanced pFe3+ Values".
Bioorganic and Medicinal Chemistry, vol. 9, 2001, pp. 563-573, XP001121004 p. 570, col. 1, paragraph 2, - col. 4, paragraph 4.

*Primary Examiner*—Kamal A. Saeed
(74) *Attorney, Agent, or Firm*—Ostrolenk, Faber, Gerb & Soffen, LLP

(57) ABSTRACT

Compounds of general formula (I), in which Het represents a five or six membered saturated, partially unsaturated or aromatic ring containing between one and six heteroatoms of the group N, O, S, in which the heterocycle is substituted in an adjacent manner with $-P-Q^i-T-Q^2$, -GZ and Y, such that the substituant -GZ is adjacent to both, the other substituants being as defined in the description, process for preparing this compound, fungicidal composition comprising this compound, method for treating plants by applying this compound or composition (I)

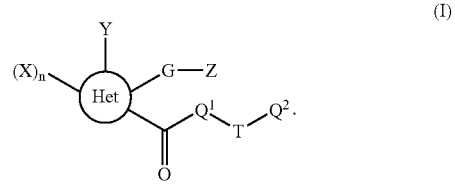

13 Claims, No Drawings

HETEROCYCLIC CARBOXAMIDES AND THEIR USE AS FUNGICIDES

CROSS REFERENCE TO RELATED APPLICATION

The present application is a 35 U.S.C. § 371 national phase conversion of PCT/EP02/08666, filed Jul. 8, 2002, which claims priority of European Application No. 01420154.5 filed Jul. 10, 2001.

The present invention relates to new substituted heterocycles, their process of preparation, their use as fungicides, particularly in the form of fungicidal compositions, and methods for the control of phytopathogenic fungi of plants using these compounds or their compositions.

Substituted heterocycles with fungicidal action are known in the literature. Thus, substituted heterocycles, disclosed in particular in patent application WO-A2-01/05769 and by M. Shimano et al. (*Tetrahedron Lett.* 1998, 12745–12774), are presented as being effective against phytopathogenic fungi of plants. These compounds, and also those disclosed in patent WO-A2-01/143339, only present heterocycles that are substituted in an adjacent manner by a) amide, b) hydroxy (or a processor thereof and c) eventually an alkoxy (or thioalkoxy) radical.

Patent application WO-A-00/26191 presents picolinamide derivatives that are optionally substituted in position 4 with a methoxy radical. Patent application WO-A-95/25723 proposes 3-pyridylcarboxylic acid derivatives.

Picolinamide derivatives are also known from patent application JP-11 228 542. These derivatives are presented as having potential antifungal activities and low toxicity, for use in pharmaceutical products.

Other picolinic acid derivatives are also known from patent application EP-A-0 690 061, in which such compounds are used as synthetic intermediates for the preparation of pyridothiadiazoles.

However, some of these known compounds have the drawback of being toxic products, which forbids any use of these compounds in agriculture for eradicating phytopathogenic diseases of crops. Others of these compounds are obtained from fermentation musts and have relatively complex chemical structures. Thus, the preparation and purification of these compounds remain demanding and expensive operations, making any industrial synthesis or marketing economically non-viable.

We have now found a new family of heterocyclic carboxamide derivative which do not possess the above mentioned drawbacks and which have an improved fungicidal activity.

Accordingly, the present invention provides heterocyclic carboxamide derivative of general formula (I):

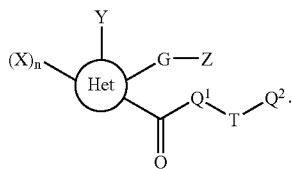

in which:

Het represents a five or six membered saturated or partially unsaturated or aromatic ring containing one or two heteroatoms of the group N, O, and S which can be identical or different, in which the heterocycle is substituted by —(C=O)-$Q^1$-T-$Q^2$, -Gz and Y in an adjacent manner, such that the substituent -Gz is adjacent to both Y and —(C=O)-$Q^1$-T-$Q^2$ and that —(C=O)-$Q^1$-T-$Q^2$, -Gz and Y are not linked with heteroatoms of Het;

n represents 0, 1, 2 or 3;

X is chosen in the group consisting of hydrogen, halogen, —$R^1$ and —$SR^1$;

Y is chosen in the group consisting of

—(C=O)—$R^3$, —$NH_2$, —$NHR^1$, —NH—(C=O)—$R^2$, —($SO^3$)—$R^1$ and O;

G is chosen in the group consisting of —$(CH_2)_k$—, —O—, —O—(C=O)— and —O—(C=O)—O—;

z is chosen in the group consisting of hydrogen, —$R^1$ and halogen;

$Q^1$ is chosen in the group consisting of

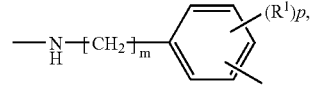

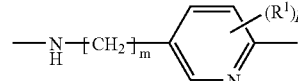

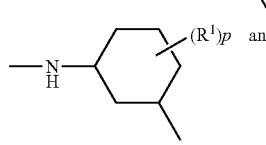 and 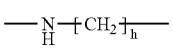

T is chosen in the group consisting of —O—, —$(CH_2)_q$— and —S—;

$Q^2$ is chosen in the group consisting of hydrogen, —$R^1$, —$R^4$, methylbenzothiazolyl,

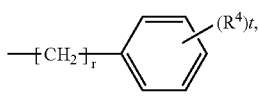 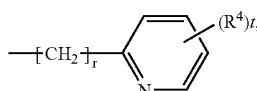

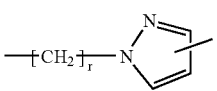 and 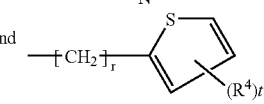

j, k, m, p, q, r and t are independently chosen as being 0, 1, 2 or 3;

h represents an integer between 0 and 10;

$R^1$ is $C_1$–$C_4$ alkyl or $C_1$–$C_4$ alkoxyalkyl;

$R^2$ is oxy-($C_1$–$C_4$)alkylene or oxy-($C_1$–$C_4$)alkyl;

$R^3$ is —OH, —$NH_2$, oxy-($C_1$–$C_4$)alkyl or oxy-($C_1$–$C_4$) alkoxyalkyl;

and $R^4$ is halogen, alkyl or halogenoalkyl;

as well as N-oxides, geometrical and/or optical isomers, enantiomers and/or diastereoisomers, tautomeric forms, salts and metal and metalloid complexes thereof, with proviso that —(C=O)-$Q^1$-T-$Q^2$ is not in the 2-position when Het represents a pyridine.

The tautomeric forms of the compound of general formula (I) are also included in the present invention. By tautomeric forms it is to be understood all of the isomeric forms well known in the art and as described in the work "The Tautomerism of Heterocycles, Advances in Heterocyclic Chemistry, Supplement 1, by J Elguero, C. Martin, A. R. Katritsky and P Linda, published by Academic Press, New York, 1976, pages 1–4.

The compound of general formula (I) can exist in one or more forms of geometrical isomers according to the number of double bonds in the compound. For example, compounds of general formula (I) can comprise 2 different geometrical isomers denoted (E) or (Z) depending on the configuration of the two double bonds. The E and Z notation can be replaced, respectively, by the term "syn" and "anti", or "cis" and "trans". Reference is made particularly to the work of E. Eliel and S. Wilen "Stereochemistry of Organic Compounds", published by Wiley (1994), for the description and use of these notations.

"Het" of the compound of general formula (I) may be a five membered ring heterocycle. Preferably, "Het" is chosen in the group consisting of thiophene, pyrrole, isoxazole, isothiazole, pyrazole and pyrrolidine.

Specific examples of compounds of the present invention where Het is a five membered heterocycle include
Het is thiophene,
n represents 0 or 1;
X is —H;
Y is chosen in the group consisting of —$NH_2$, —$CO_2H$, —NHC(O)$R^2$ and —S(O)$_2$—$R^1$;
$R^1$ is $C_1$–$C_4$ alkyl;
$R^2$ is oxy-($C_1$–$C_4$)alkylene;
G is —O—;
Z is —H or —$R^1$;
$Q^1$ is

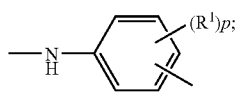

T is —O— or —($CH_2$)$_q$—;
$Q^2$ is chosen in the group consisting of:

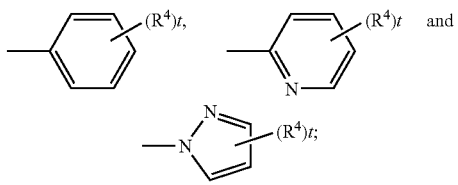

p and t are independently chosen as being 0, 1 or 2;
q is 0;

as well as the optional N-oxides, geometrical and/or optical isomers, enantiomers and/or diastereoisomers, tautomeric forms, salts and metal and metalloid complexes thereof.

A further example is where
Het is pyrrole;
n represent 0, 1 or 2;
X is —H or —$R^1$;
Y is chosen in the group consisting of —$NH_2$, —C(O)$R^3$, —NHC(O)$R^2$ and —S(O)$_2$—$R^1$;
$R^1$ is $C_1$–$C_4$ alkyl;
$R^2$ is oxy-($C_1$–$C_4$)alkylene;
$R^3$ is —OH, oxy-($C_1$–$C_4$)alkyl or oxy-($C_1$–$C_4$)alkoxyalkyl;
G is —O—;
Z is —H or —$R^1$;
p and t are independently chosen as being 0, 1 or 2;
$Q^1$ is

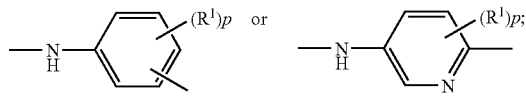

T is —O— or —($CH_2$)$_q$—;
q is 0;
$Q^2$ is chosen in the group consisting of hydrogen, —$R^1$, —$R^4$,

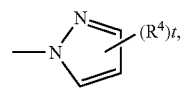

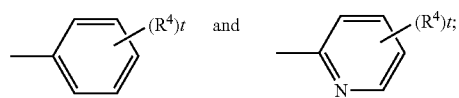

as well as the optional N-oxides, geometrical and/or optical isomers, enantiomers and/or diastereoisomers, tautomeric forms, salts and metal and metalloid complexes thereof.

A further example is where:
Het is isoxazole;
n is 0;
Y is chosen in the group consisting of —$NH_2$, —C(O)$R^3$, —NHC(O)$R^2$ and —S(O)$_2$—$R^1$;
$R^1$ is $C_1$–$C_4$ alkyl;
$R^2$ is oxy-($C_1$–$C_4$)alkylene or oxy-($C_1$–$C_4$)alkyl;
$R^3$ is —OH, oxy-($C_1$–$C_4$)alkyl or oxy-($C_1$–$C_4$)alkoxyalkyl;
G is —O—;
Z is —H;
p and t are independently chosen as being 0, 1 or 2;
$Q^1$ is

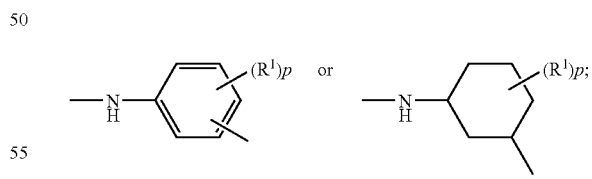

T is —O— or —($CH_2$)$_q$—;
q is 0;
$Q^2$ is chosen in the group consisting of

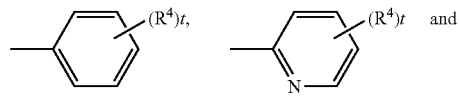

-continued

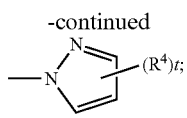

as well as the optional N-oxides, geometrical and/or optical isomers, enantiomers and/or diastereoisomers, tautomeric forms, salts and metal and metalloid complexes thereof.

A further example is where:
Het is pyrrolidin;
n is 1 or 2;
Y is O;
G is —O—;
Z is —H;
p and t are independently chosen as being 0, 1 or 2;
$Q^1$ is

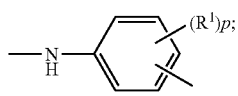

T is —O— or —(CH$_2$)$_q$—;
q is 0;
$Q^2$ is chosen in the group consisting of hydrogen, —R$^1$, —R$^4$,

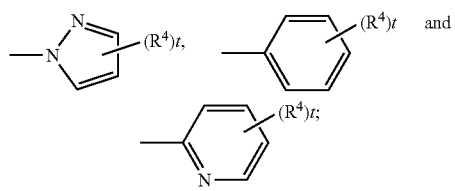

as well as the optional N-oxides, geometrical and/or optical isomers, enantiomers and/or diastereoisomers, tautomeric forms, salts and metal and metalloid complexes thereof "Het" of the compound of general formula (I) may be a six membered ring heterocycle. Preferably, Het is chosen in the group consisting of pyridine, such that —(C═O)-Q$^1$-T-Q$^2$ is attached in 3-position, 1,2-pyridazine, such that —(C═O)-Q$^1$-T-Q$^2$ is attached in 3-position and pyranone, such that —(C═O)-Q$^1$-T-Q$^2$ is attached in 2-position.

Specific examples of compounds of the present invention where Het is a six membered heterocycle include:
Het is pyridine, such that —(C═O)-Q$^1$-T-Q$^2$ is attached in 3-position;
n represent 0, 1 or 2;
X is —H or —R$^1$;
Y is chosen in the group consisting of

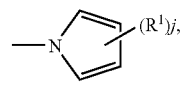

—(C═O)—R$^3$, —NH$_2$, —NHR$^1$, —NH—(C═O)—R$^2$, —(SO$^2$)—R$^1$ and —O;
R$^1$ is C$_1$–C$_4$ alkyl;
R$^2$ is oxy-(C$_1$–C$_4$)alkylene or oxy-(C$_1$–C$_4$)alkyl;

R$^3$ is —OH, oxy-(C$_1$–C$_4$)alkyl or oxy-(C$_1$–C$_4$)alkoxyalkyl;
G is —O—;
Z is —H or —R$^1$;
p and t are independently chosen as being 0, 1 or 2;
$Q^1$ is

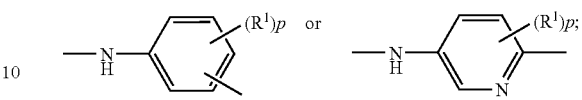

T is —O— or —(CH$_2$)$_q$—;
q is 0,;
$Q^2$ is chosen in the group consisting of:

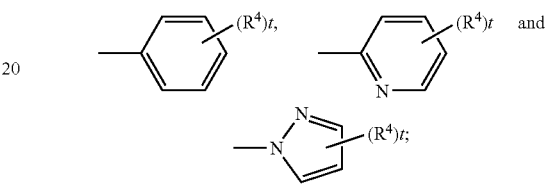

as well as the optional N-oxides, geometrical and/or optical isomers, enantiomers and/or diastereoisomers, tautomeric forms, salts and metal and metalloid complexes thereof.

A further example is where:
Het is pyranone, such that —(C═O)-Q$^1$-T-Q$^2$ is attached in 2-position;
n is 0, 1 or 2;
X is —H or —R$^1$;
Y is O;
R$^1$ is C$_1$–C$_4$ alkyl;
G is —O—;
Z is —H;
p, q and t are independently chosen as being 0, 1 or 2;
$Q^1$ is

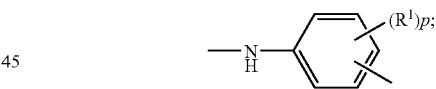

T is —O— or —(CH$_2$)$_q$—;
$Q^2$ is chosen in the group consisting of

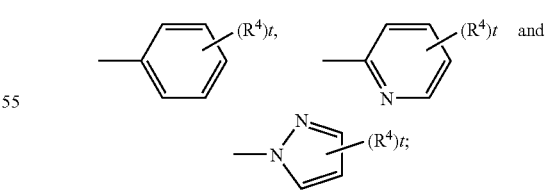

as well as the optional N-oxides, geometrical and/or optical isomers, enantiomers and/or diastereoisomers, tautomeric forms, salts and metal and metalloid complexes thereof.

The compound of general formula (I) can exist in one or more optical isomeric or chiral forms according to the number of asymmetric centres in the compound. The present invention thus also includes all the optical isomers and their racemic or scalemic (scalemic designates a mixture of enantiomers in different proportions), as well as the mixtures of all possible stereoisomers in all proportions, including the racemic mixture. The separation of the diastereoisomers and/or optical isomers can be effected by known methods (E. Eliel ibid.).

The present invention also relates to the process of preparation of the compound of general formula (I). Thus, according to a further aspect of the present invention there is provided a process for the preparation of compound of general formula (I) as defined above, which process is defined by scheme I:

Scheme 1

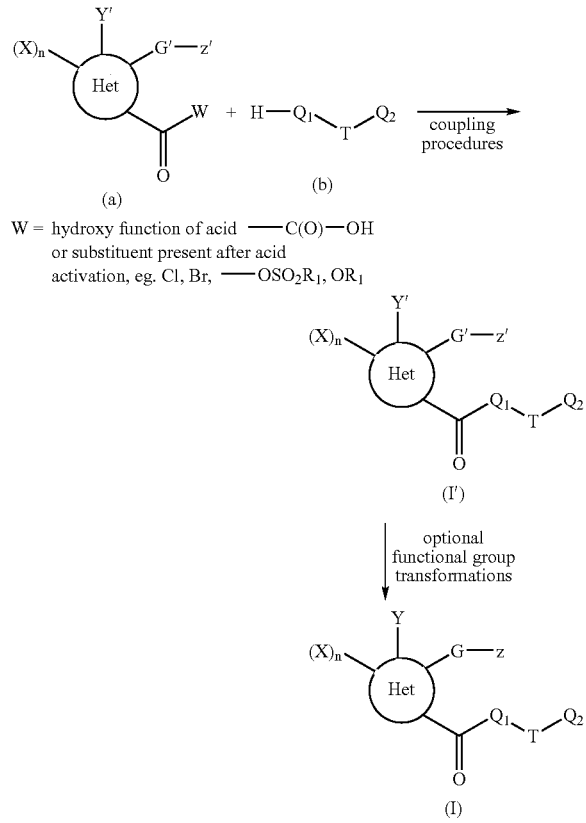

by effecting a reaction between a substituted heterocyclic acid or acid derivative of general formula (a) with a nucleophilic compound of general formula (b), wherein:
Y' chosen in the group consisting of

halogen, —$NH_2$, —$NO_2$, —(C=O)—$R^3$, —$NHR^1$, —NH—(C=O)—$R^2$, —($SO_2$)—$R^1$ and O;
G' is chosen in the group consisting of —$(CH_2)_k$—, —O—, —O—(C=O)— and —O—(C=O)—O—;
z' is chosen in the group consisting of hydrogen, —$R^1$, halogen and benzyl;
Y', G' and z' may also form a substituted oxazolic ring degradable to Y=$NH_2$ and G-z=OH;
X, Y, G, z, $Q^1$, T, $Q^2$ are as defined above;

W represents a hydroxy group (—OH) present in the free acid —(C=O)—OH or a group obtained after activation of the free acid —(C=O)—OH.

With regard to W of the compound of general formula (a), suitable examples of the group obtained after activation of the free acid —(C=O)—OH include halo radical, alkylcarbonyloxy or alkylsulphonyloxy.

Compound of the general formula (I') may optionally be converted to compound of general formula (I) via some well known functional group transformations, such as:
reduction of a nitro group to an amino group with hydrogen in a presence of a catalyseur such as platinum or palladium on charcoal in a protic solvent such as methanol under pressure;
deprotection of a protected amino or hydroxyl group to the free amino or hydroxyl using acidic (such as boron tribromide in dichloromethane or aqueous hydrochloric acid) or basic (sodium or potassium hydroxyde aqueous solution) conditions;
substitution of a leaving group such as halide by a suitable nucleophile in the presence of a base in an aprotic solvent;
Curtius or Hofmann rearrangement as described by Banthorpe in *The chemistry of the azido group* (1971) pp 397, or by Wallis in *Organic Reactions* (1946) pp 267.

The compound according to the present invention can be prepared according to the general method of preparation described above. It will nevertheless be understood that the skilled worker will be able to adapt this method according to the specifics of each of the compounds, which it is desired to synthesise.

The preparation of reagents used in one or other of the general methods of preparation is generally known and is generally described specifically in the prior art or in such a manner that the man skilled in the art can adapt it to the desired aim. The prior art usable by the normally skilled worker in order to establish conditions for the preparation of reagents can be found in numerous general chemistry text books such as "Advanced Organic Chemistry" by J. March, published by Wiley (1992), "Methoden der organischen Chemie" (Houben-Weyl), published by Georg Thieme Verlag or the "Chemical Abstracts" published by the American Chemical Society as well as in information data bases accessible to the public.

The reactants in the above process are commercially available or readily available utilising standard procedures.

The heterocyclic acids of general formula (a) may be obtained in the form of their alkylesters. In this case, the compounds are saponified according to standard deprotection procedures as described by or referenced in T. W. Greene, P. W. Greene, "*Protective Groups in Organic Synthesis*", Wiley & Sons, New York 1991. Subsequently, the heterocyclic acid or an acid derivative obtained from the acid is reacted with an amine according to known coupling procedures as published in Houben-Weyl, "Methoden der Organischen Chemie", Eugen Müller (Ed.), Thieme Publisher, Stuttgart. Subsequently, some substituants on the heterocylic carboxamide may optionally be subjected to functional group transformations as described or referenced in R. C. Larock, "*Comprehensive Organic Transformations*", VCH Publishers, Weinheim, 1989 or in computerised reaction databases like e.g. "Beilstein Commander 2000, Version 5.0", provided by MDL databases, to give another compound of the general formula (I).

The present invention also relates to fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support.

In the present specification, the term "support" denotes a natural or synthetic, organic or inorganic material with which the active material is combined to make it easier to apply to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be between 5% and 40% by weight.

Additional but optional components also include protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention usually may contain from 0.05 to 99% (by weight) of active material, preferably 10 to 70% by weight.

Compositions according to the present invention can be used in quite diverse forms such as aerosol dispenser, bait(ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The compounds of the invention can also be mixed with one or more insecticides, fungicides, bactericides, attractant acaricides or pheromones or other compounds with biological activity. The mixtures thus obtained have a broadened spectrum of activity. In particular the compounds of the present invention do not exhibit the problem of cross-resistance with strobilurin derivatives. In fact the compounds of the present invention are active on a different biochemical site to strobilurin derivatives.

The mixtures with other fungicides are particularly advantageous, especially the mixtures with acibenzolar-S-methyl, benalaxyl, benomyl, blasticidin-S, bromuconazole, captafol, captan, carbendazim, carboxin, carpropamide, chlorothalonil, fungicidal compositions based on copper, derivatives of copper such as copper hydroxide and copper oxychloride, cyazofamide, cymoxanil, cyproconazole, cyprodinil, dichloran, diclocymet, diethofencarb, difenoconazole, diflumetorim, dimethomorph, diniconazole, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, mancozeb, maneb, mefenoxam, mepanipyrim, metalaxyl and their enantiomeric forms such as metalaxyl-M, metconazole, metiram-zinc, oxadixyl, pefirazoate, penconazole, pencycuron, phosphorous acid and its derivatives such as fosetyl-Al, phthalide, probenazole, prochloraz, procymidone, propamocarb, propiconazole, pyrimethanil, pyroquilon, quinoxyfen, silthiofam, simeconazole, spiroxamine, tebuconazole, tetraconazole, thiabendazole, thifluzarnide, thiophanate, for example thiophanate-methyl, thiram, triadimefon, triadimenol, triazolopyrimidines e.g. cloransulam-methyl, flumetsulam, florasulam, metosulam, tricyclazole, tridemorph, trifloxystrobin, triticonazole, derivatives of valinamide such as for example, iprovalicarb and benthiavalicarb, vinclozolin, zineb and zoxamide, as well as fungicide of the strobilurin familly, for example azoxystrobin, kresoxym-methyl, metominostrobin, discostrobin, dimoxystrobin, picoxystrobin, pyraclostrobin, and trifloxystrobin.

The fungicidal compositions of the present invention can be used to curatively or preventively combat the phytopathogenic fungi of crops. Thus, according to a further aspect of the present invention, there is provided a method for curatively or preventively combating the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers and rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants targeted by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae.* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants targeted by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma specie tritici*), rusts (*Puccinia strhiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma specie hordei*), dwarf leaf rust (*Puccinia hordei*) and leaf blotch (*Rhynchosporium secalis*);

potato, as regards controlling tuber diseases (in particular *Heiminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: darnping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), altermaria leaf spot (*Alternaria* sp.), anthracnose (*Colletoirichum* sp.), septoria leaf spot (*Septoria* sp.), black speck (*Rhizoctonia solani*), mildews (for example *Bremia lactucae, Peronospora* sp., *Pseudoperonospora* sp., *Phytophihora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

Cereals are preferably treated according to the method of the present invention. Wheat and rice are still preferred for carrying out the method according to the invention.

The fungicide composition according to the present invention may also be used against fungal diseases liable to grow on or inside lumber. The term "lumber" means all types of species of wood, and all types of working of this wood intended for construction, for example solid wood, high-density wood, laminated wood, and plywood. The method for treating lumber according to the invention consists in placing one or more compounds of the present invention, or a composition according to the invention, in contact. This placing in contact may cover the most diverse of forms such as, for example, direct application, spraying, dipping, injection or any other suitable means.

The dose of active material applied in the treatment according to the present invention is generally and advantageously between 10 and 800 g/ha, preferably between 50 and 300 g/ha for applications in foliar treatment. The dose of active material applied is generally and advantageously between 2 and 200 g per 100 kg of seed, preferably between 3 and 150 g per 100 kg of seed in the case of seed treatments. It is clearly understood that the doses indicated above are given as illustrative examples of the invention. A person skilled in the art will know how to tailor the application doses according to the nature of the crop to be treated.

The fungicidal composition according to the present invention may also be used in the treatment of genetically modified plants with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

Among the genes which give the transformed plants new agronomic properties, mention may be made of genes which impart a tolerance to certain herbicides, those which impart a resistance to certain insects, those which impart a tolerance to certain diseases, etc. Such genes are described in particular in patent applications WO 91/02071 and WO 95/06128.

Among the genes which impart a tolerance to certain herbicides, mention may be made of the Bar gene imparting tolerance to bialophos, the gene encoding a suitable EPSPS imparting a resistance to herbicides having EPSPS as target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435 and FR 2 736 926), the gene encoding glyphosate oxidoreductase (U.S. Pat. No. 5,463,175) or a gene encoding an HPPD imparting a tolerance to herbicides having HPPD as target, such as isoxazoles, in particular isoxafutol (FR 95/06800 and FR 95/13570), diketonitriles (EP-A-0 496 630 and EP-A-0 496 631) or triketones, in particular sulcotrione (EP-A-0 625 505, EP-A-0 625 508 and U.S. Pat. No. 5,506,195). Such genes encoding an HPPD imparting a tolerance to herbicides having HPPD as target are disclosed in patent application WO 96/38567. In the case of genes encoding EPSPS or HPPD, and more particularly for the above genes, the sequence encoding these enzymes is advantageously preceded by a sequence encoding a transit peptide, in particular for the transit peptide known as optimized transit peptide, disclosed in patent U.S. Pat. No. 5,510,471.

Among the genes imparting novel insect-resistance properties, mention will be made more particularly of the genes encoding the Bt proteins which are widely described in the literature and well known to those skilled in the art. Mention will also be made of the genes encoding proteins extracted from bacteria such as *Photorabdus* (WO 97/17432 and WO 98/08932).

Among the genes imparting novel disease-resistance properties, mention will be made in particular of the genes encoding chitinases, glucanases and oxalate oxidase, all these proteins and their coding sequences being widely described in the literature, or genes encoding antibacterial and/or antifungal peptides, in particular cysteine-rich peptides containing less than 100 amino acids, such as plant thionines or defensines, and more particularly lytic peptides of all origins comprising one or more disulphide bridges between the cysteines and regions comprising basic amino acids, in particular the following lytic peptides: androctonine (WO 97/30082 and PCT/FR98/01814, filed on 18 Aug. 1998) or drosomicin (PCT/FR98/01462, filed on 8 Jul. 1998). Mention will also be made of the genes encoding fungal elicitor peptides, in particular the elicitins (Kamoun et al., 1993; Panabières et al., 1995).

Among the genes which modify the constitution of modified plants, mention may be made in particular of genes which modify the content and quality of certain essential fatty acids (EP-A-0 666 918) or the content and quality of proteins, in particular in the leaves and/or seeds of the said plants. Mention will be made in particular of the genes encoding proteins that are rich in sulphur-containing amino acids (WO 98/20133; WO 97/41239; WO 95/31554; WO 94/20828 and WO 92/14822).

The fungicidal composition according to the present invention may, in particular, be used to the treatment of genetically modified plants comprising a heterologous gene, which gives the plant disease-resistance properties. The heterologous gene preferentially gives the genetically modified plant a spectrum of activity that is complementary to the spectrum of activity of the compounds according to the invention. According to the invention, the expression "complementary spectrum" means a spectrum of activity for the heterologous gene which is different from the spectrum of activity of the compounds according to the invention, or a spectrum of activity relating to identical infectious agents but allowing an identical or improved control for lower application doses of compounds according to the invention.

The compositions according to the present invention may also be used used to curatively or preventively treat human and animal fungal diseases such as, for example, mycoses, dermatoses, trichophyton diseases and candidiases or diseases caused by *Aspergillus* spp., for example *Aspergillus fumigatus*.

The aspects of the present invention will now be illustrated with reference to the following tables of compounds and examples. The following Tables I to XII illustrate in a non-limiting manner examples of fungicidal compounds according to the present invention. In the following Examples, "MP" signifies "melting point" and is expressed in ° Celsius (° C.). M+1 (or M−1) means the molecular ion peak, plus or minus 1 a.m.u. (atomic mass units) respectively, as observed in mass spectroscopy.

TABLE I

THIOPHENE DERIVATIVES

| N° | X1 | Y | G | Z | Q1 |
|---|---|---|---|---|---|
| 1 | H | H₂N– | –O– | H | –NH–C₆H₄– |
| 2 | H | allyl-O-C(O)-NH– | –O– | H | –NH–C₆H₄– |
| 3 | H | HOOC-C(CH₃)– | –O– | H | –NH–C₆H₄– |
| 4 | H | CH₃-S(O)₂– | –O– | H | –NH–C₆H₄– |

| N° | T | Q2 | ion mol. | MP |
|---|---|---|---|---|
| 1 | –O– | 4-CF₃-C₆H₄– | M + 1 = 395 | |
| 2 | –O– | 4-CF₃-C₆H₄– | M + 1 = 493 | |
| 3 | –O– | 4-CF₃-C₆H₄– | M + 1 = 438 | |

TABLE I-continued
| | | | |
|---|---|---|---|
| 4 | —O— | 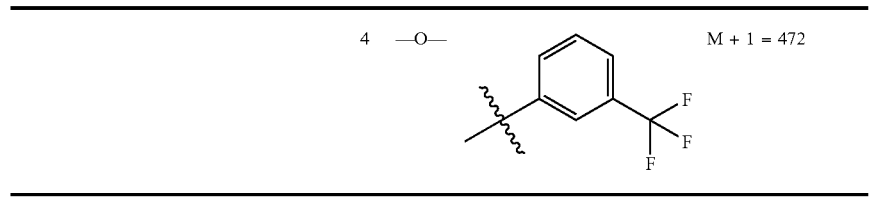 | M + 1 = 472 |
TABLE II
PYRROLE DERIVATIVES
| N° | X2 | X1 | Y | G | Z | Q1 |
|---|---|---|---|---|---|---|
| 5 | | H | allyl carbamate | —O— | | NH-phenyl |
| 6 | | H | allyl carbamate | —O— | | NH-phenyl |
| 7 | | H | ethyl carbamate | —O— | | NH-phenyl |
| 8 | | H | allyl carbamate | —O— | | NH-phenyl |
| 9 | | H | H₂N | —O— | H | NH-phenyl |

TABLE II-continued

| N° | T | Q2 | ion mol. MP |
|---|---|---|---|
| 5 | —O— | 4-(trifluoromethyl)phenyl | M + 1 = 490 |
| 6 | —O— | 3-(trifluoromethyl)phenyl | M + 1 = 490 |
| 7 | —O— | 3-(trifluoromethyl)phenyl | M + 1 = 478 |
| 8 | —O— | pentyl | M + 1 = 402 |
| 9 | —O— | pentyl | M + 1 = 304 |

TABLE III

PYRROLE DERIVATIVES

| N° | X2 | X1 | Y | G | Z | Q1 |
|---|---|---|---|---|---|---|
| 10 | methyl | H | ethyl 2-propanoate | —O— | H | 4-substituted anilino (NH-phenyl) |

TABLE III-continued
| | | | | | | |
|---|---|---|---|---|---|---|
| 11 |  |  | 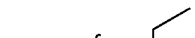 | —O— |  | 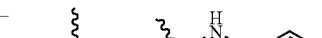 |
| 12 |  |  |  | —O— |  |  |
| 13 |  |  |  | —O— |  | 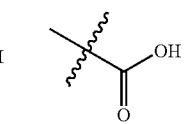 |
| 14 |  | 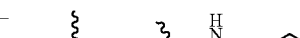 |  | —O— |  |  |
| 15 |  |  | 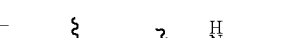 | —O— |  |  |
| 16 |  | 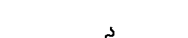 |  | —O— |  |  |
| 17 |  |  |  | —O— |  |  |
| 18 |  |  |  | —O— |  |  |
| N° | T | Q2 | ion mol. | MP |
|---|---|---|---|---|
| 10 |  |  | M + 1 = 289 | |
| 11 | —O— |  | M + 1 = 319 | |

TABLE III-continued
| | | | |
|---|---|---|---|
| 12 | —O— | 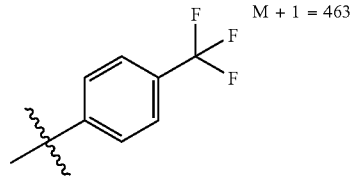 | M + 1 = 463 |
| 13 | —O— | 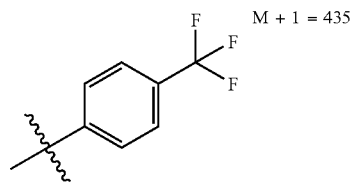 | M + 1 = 435 |
| 14 | —O— | 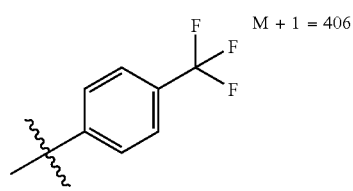 | M + 1 = 406 |
| 15 | —O— | 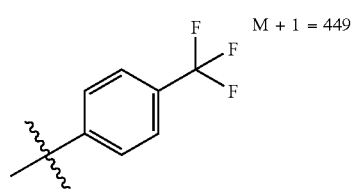 | M + 1 = 449 |
| 16 | —O— | 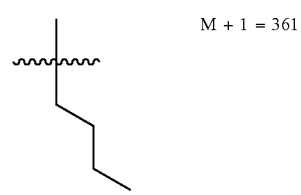 | M + 1 = 361 |
| 17 | —O— | 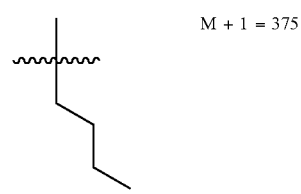 | M + 1 = 375 |
| 18 | —O— | 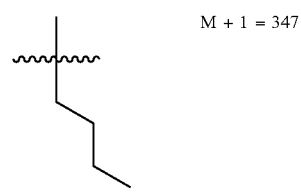 | M + 1 = 347 |

TABLE IV

PYRIDINE DERIVATIVES

| N° | X1 | X2 | Y | G | Z | Q1 |
|----|----|----|---|---|---|----|
| 19 | H | H | NH₂ | —O— | H | —NH—C₆H₄— (para) |
| 20 | H | H | NH₂ | —O— | H | —NH—C₆H₄— (para) |
| 21 | H | H | NH₂ | —O— | H | —NH—(3,3,5-trimethylcyclohexyl)— |
| 22 | H | H | NH₂ | —O— | H | —NH—C₆H₄— (para) |
| 23 | H | H | NH₂ | —O— | H | —NH—C₆H₄— (para) |
| 24 | H | H | NH₂ | —O— | H | —NH—C₆H₄— (para) |
| 25 | H | H | NH₂ | —O— | H | —NH—(2-methyl-C₆H₃)— (1,4) |

TABLE IV-continued

| N° | T | Q2 | ion mol. MP |
|---|---|---|---|
| 19 | —O— | 4-CF3-phenyl | M − 1 = 388 |
| 20 | —O— | n-pentyl | M + 1 = 302 |
| 21 | | —H | M + 1 = 278 |
| 22 | —O— | 4-methylphenyl | M + 1 = 336 |
| 23 | —O— | 3-CF3-phenyl | M + 1 = 390 |
| 24 | —O— | 3-Cl-4-CF3-phenyl | M + 1 = 424 |
| 25 | —O— | 4-CF3-phenyl | |

TABLE IV-continued
| N° | | | |
|---|---|---|---|
| 26 | —O— | 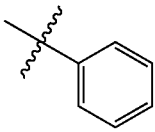 | |
| 27 | —O— | 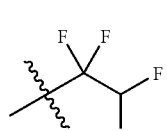 | M + 1 = 346 |
TABLE V
ISOXAZOLE DERIVATIVES
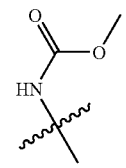
| N° | Y | G | Z | Q1 |
|---|---|---|---|---|
| 28 | 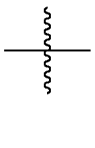 | —O— | 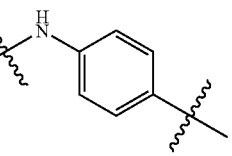 | 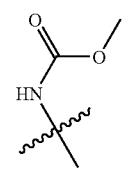 |
| 29 | 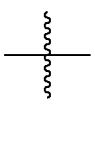 | —O— | 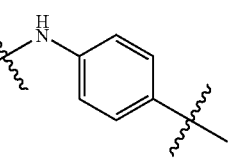 | 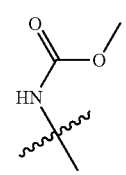 |
| 30 | 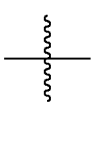 | —O— | 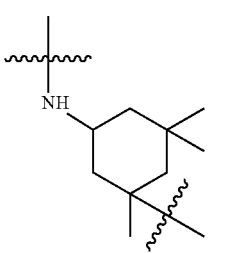 | 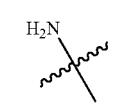 |
| 31 | 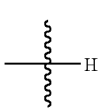 | —O— | ⸺H | 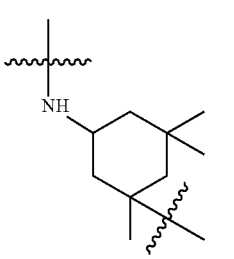 |

TABLE V-continued
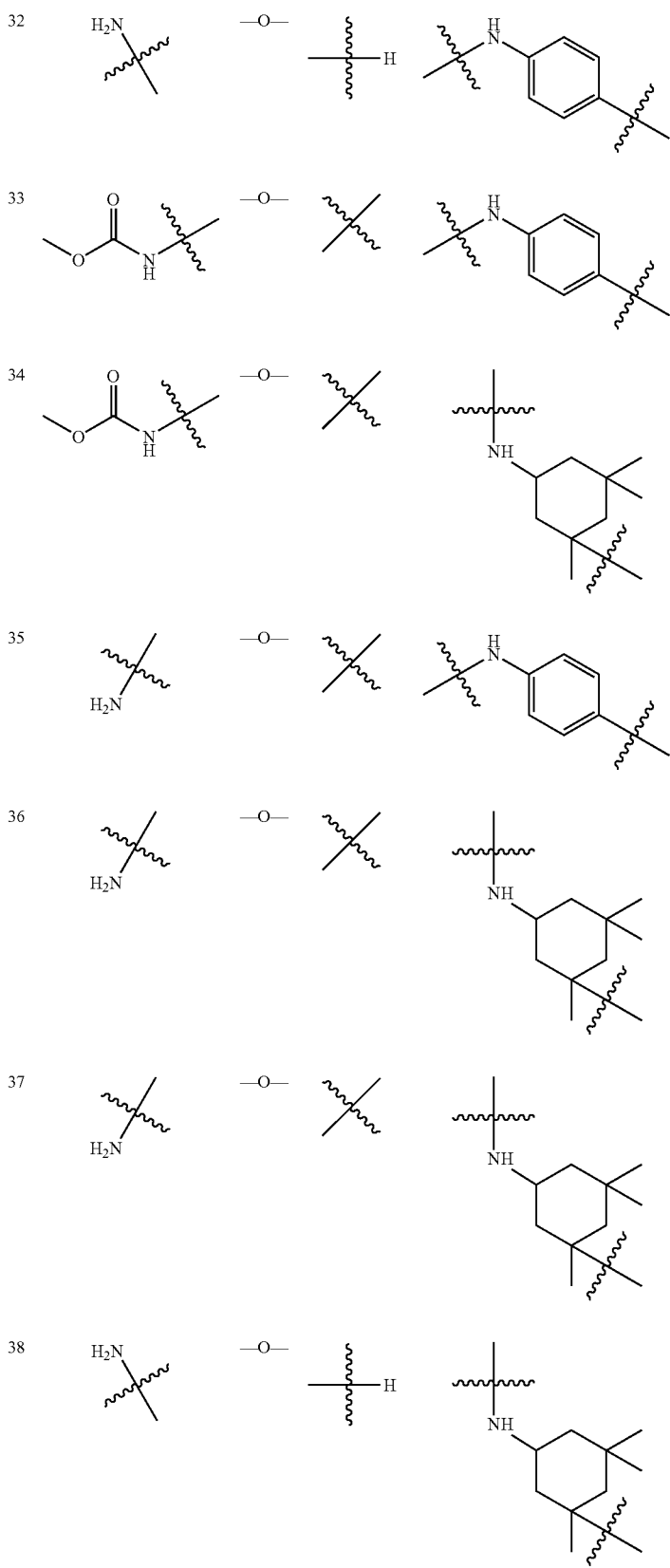

TABLE V-continued
| N° | T | Q2 | ion mol. | MP |
|---|---|---|---|---|
| 28 | —O— | 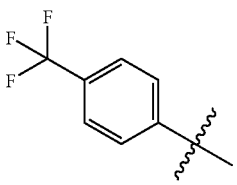 | M + 1 = 452 | |
| 29 | —O— | 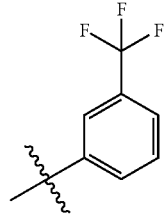 | M + 1 = 452 | |
| 30 |  |  | M + 1 = 368 | 172 |
| 31 | 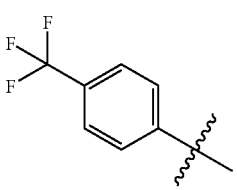 | 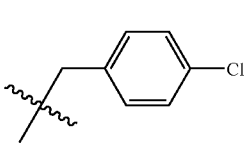 | M + 1 = 296 | 208 |
| 32 | —O— |  | M + 1 = 380 | |
| 33 | —O— | 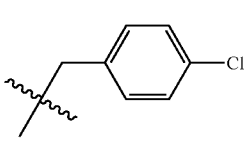 | M + 1 = 432 | |
| 34 | 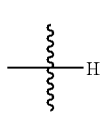 | —H | M + 1 = 340 | |
| 35 | —O— | 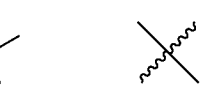 | M + 1 = 374 | |
| 36 | 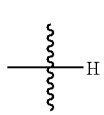 | —H | M + 1 = 282 | |
| 37 |  |  | M + 1 = 310 | |
| 38 | 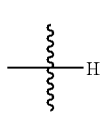 | —H | M + 1 = 268 | |

TABLE VI

ISOXAZOLE DERIVATIVES

| N° | Y | G | Z | Q1 | T | Q2 | ion mol. | MP |
|---|---|---|---|---|---|---|---|---|
| 39 | -C(CH₃)₂-C(O)OCH₃ | —O— | -C(CH₃)₂- | -NH-C₆H₄- | —O— | -C₆H₄-CF₃ | M + 1 = 437 | |
| 40 | -C(CH₃)₂-C(O)OH | —O— | -CH- | -NH-C₆H₄- | —O— | -C₆H₄-CF₃ | M + 1 = 423 | |
| 41 | -C(CH₃)₂-C(O)OCH₃ | —O— | -C(CH₃)₂- | -NH-C₆H₄- | —O— | -n-butyl | M + 1 = 349 | |

TABLE VII

ISOTHIAZOLE DERIVATIVES

| N° | Y | G | Z | Q1 | T | Q2 | ion mol. | MP |
|---|---|---|---|---|---|---|---|---|
| 42 | -NH₂ | bond | -CH- | -NH-C₆H₄- | —O— | -C₆H₄-CF₃ | M + 1 = 380 | |

TABLE VIII
PYRAZOLE DERIVATIVES

| N° | X1 | Y | G | Z | Q1 | T | Q2 | ion mol. | MP |
|----|----|----|----|----|----|----|----|----|----|
| 43 | (isopropyl) | NH₂ | —O— | H | NH-C₆H₄- | —O— | 4-CF₃-C₆H₄- | M + 1 = 393 | |
| 44 | (isopropyl) | NH₂ | —O— | H | NH-C₆H₄- | —O— | 3-CF₃-C₆H₄- | M + 1 = 393 | 134 |

TABLE IX
PYRIDINE DERIVATIVES

| N° | X1 | X2 | Y | G | Z | Q1 |
|----|----|----|----|----|----|----|
| 45 | H | H | NH₂ | —O— | H | NH-C₆H₄- |
| 46 | H | H | NH₂ | —O— | H | NH-C₆H₄- |
| 47 | (isopropyl) | (isopropyl) | NH₂ | —O— | H | NH-C₆H₄- |

TABLE IX-continued
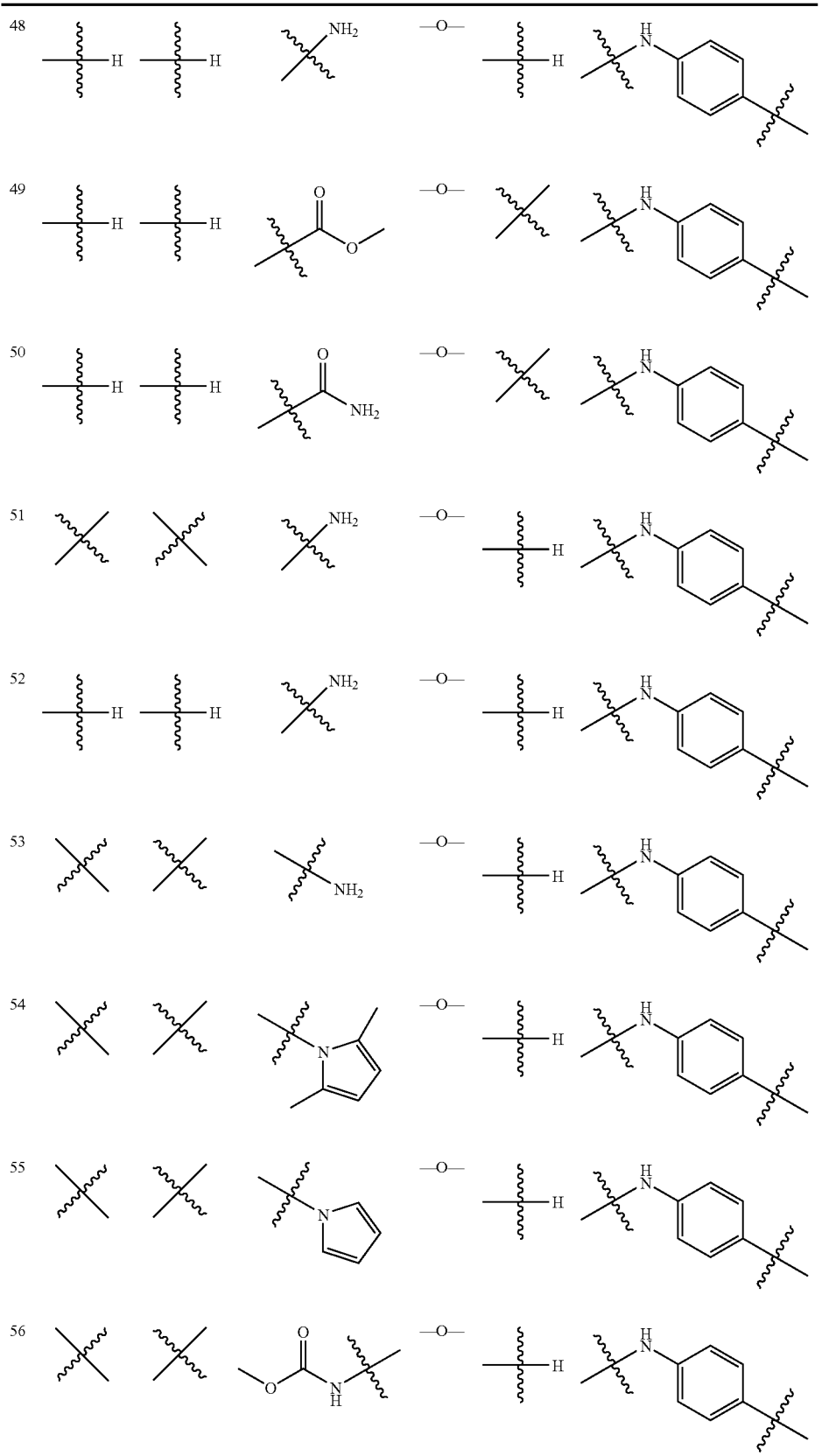

TABLE IX-continued

| N° | | | | | | |
|----|---|---|---|---|---|---|
| 57 | [structure] | [structure] | [structure with NH₂] | —O— | [structure with H] | [NH-phenyl structure] |
| 58 | [structure] | [structure] | [2,5-dimethylpyrrole structure] | —O— | [structure with H] | [NH-phenyl structure] |

| N° | T | Q2 | ion mol. | MP |
|----|---|----|----|----|
| 45 | —O— | [3-(trifluoromethyl)phenyl] | M + 1 = 388 | 166 |
| 46 | —O— | [4-(trifluoromethyl)phenyl] | M + 1 = 390 | 186 |
| 47 | —O— | [4-(trifluoromethyl)phenyl] | M + 1 = 418 | |
| 48 | [–CH₂CH₂–] | [3-(trifluoromethyl)phenyl] | M + 1 = 402 | 200 |
| 49 | —O— | [3-chloro-4-(trifluoromethyl)phenyl] | M + 1 = 481 | 164 |
| 50 | —O— | [3-chloro-4-(trifluoromethyl)phenyl] | M + 1 = 466 | 218 |

TABLE IX-continued

| | | | | |
|---|---|---|---|---|
| 51 | (CH2CH2CH2) | 3-(CF3)-phenyl | M + 1 = 430 | 232 |
| 52 | —O— | 4-methylphenyl | M + 1 = 336 | |
| 53 | —O— | CHF2CF2-C(CH3) | M + 1 = 374 | 236 |
| 54 | —O— | CHF2CF2-C(CH3) | M + 1 = 452 | |
| 55 | —O— | CHF2CF2-C(CH3) | M + 1 = 424 | |
| 56 | —O— | 4-(CF3)-phenyl | M + 1 = 476 | |
| 57 | —O— | 4-Cl-phenyl | M + 1 = 384 | |
| 58 | —O— | 4-Cl-phenyl | M + 1 = 462 | |

TABLE X

PYRANONE DERIVATIVES

| N° | X1 | X2 | Y | G | Z | Q1 |
|---|---|---|---|---|---|---|
| 59 | H | H | =O | —O— | H | -NH-C6H4- |
| 60 | H | H | =O | —O— | H | -NH-C6H4- |
| 61 | H | H | =O | —O— | H | -NH-C6H4- |
| 62 | H | H | =O | —O— | H | -NH-C6H4- |
| 63 | H | H | =O | —O— | H | -NH-C6H4- |
| 64 | H | H | =O | —O— | H | -NH-trimethylcyclohexyl |
| 65 | H | H | =O | —O— | H | -NH-(2,5-dimethylphenyl)- |

TABLE X-continued
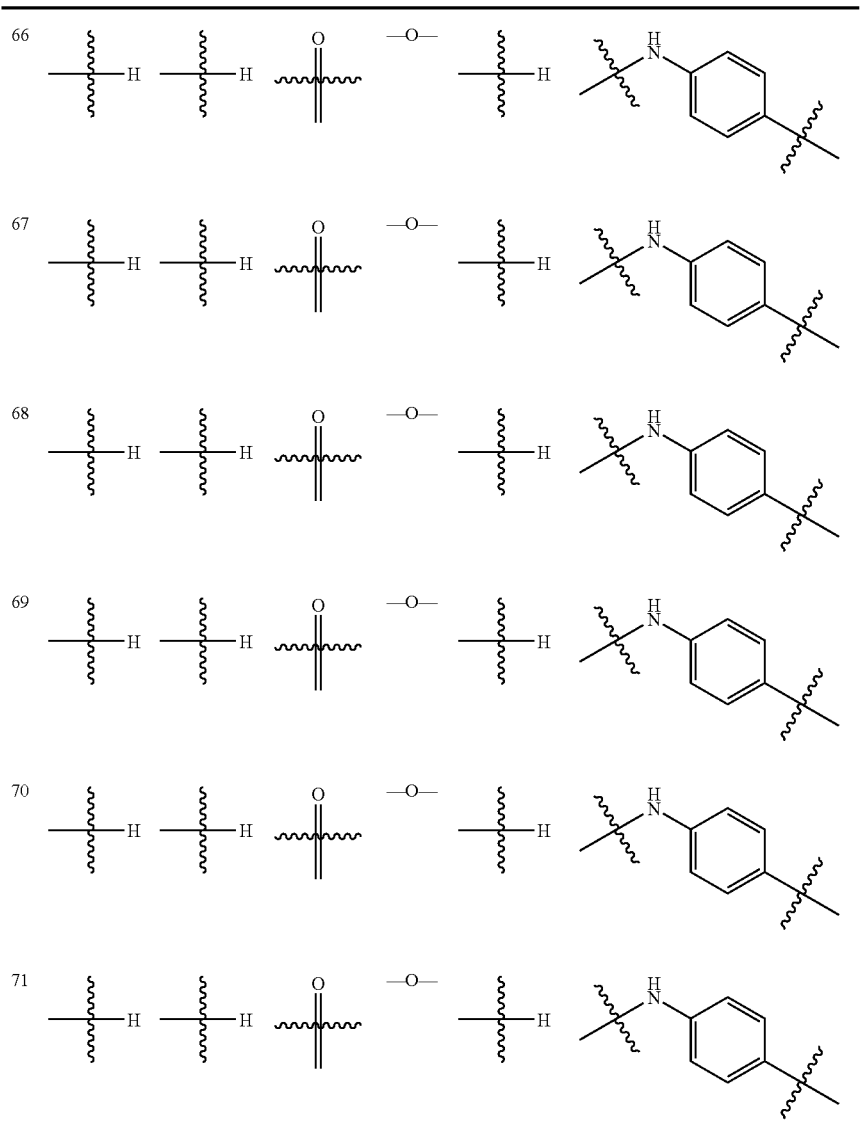
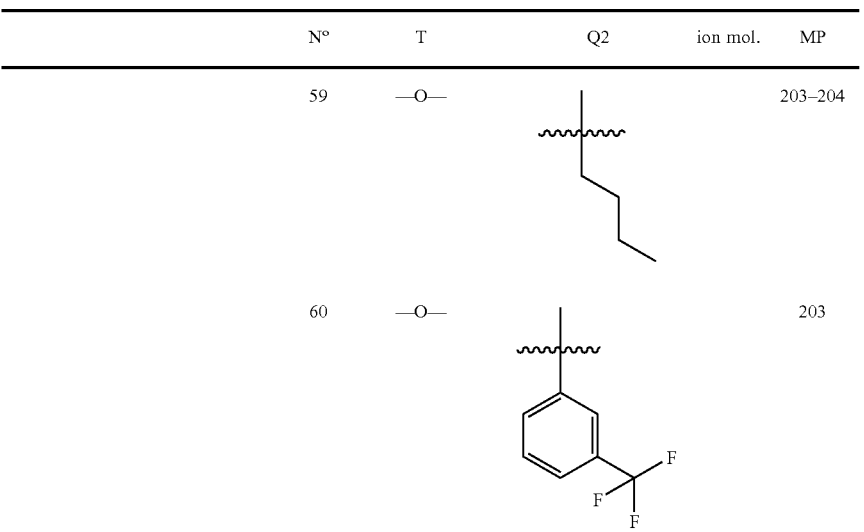

TABLE X-continued

| 61 | —O— | 4-(trifluoromethyl)phenyl |
| 62 | —O— | phenyl |
| 63 | —O— | p-tolyl (4-methylphenyl) |
| 64 | — | H |
| 65 | —S— | isopropyl |
| 66 | —O— | methyl |
| 67 | —O— | 3,3,3-trifluoropropyl (—CH₂CH(CF₃)) variant |
| 68 | —O— | 4-chlorophenyl |

TABLE X-continued

| 69 | | |
| 70 | —O— | |
| 71 | —O— | 228 |

TABLE XI

PYRROLIDINE DERIVATIVES

| N° | X1 | X2 | Y | G | Z | Q1 |
|---|---|---|---|---|---|---|
| 72 | H | (isopropyl) | (=CH₂) | —O— | H | NH-phenyl |
| 73 | H | (isopropyl) | (=O) | —O— | H | NH-phenyl |

| N° | T | Q2 | ion mol. | MP |
|---|---|---|---|---|
| 72 | —O— | phenyl | | 251 |
| 73 | —O— | 4-CF₃-phenyl | M + 1 = 421 | |

TABLE XII

PYRIDAZINE DERIVATIVES

| N° | X1 | Y | G | Z | Q1 | T | Q2 | ion mol. | MP |
|---|---|---|---|---|---|---|---|---|---|
| 74 | H | NH₂ | —O— | H | NH-C₆H₄- | —O— | 3-CF₃-C₆H₄- | | |
| 75 | H | NH₂ | —O— | H | NH-C₆H₄- | —O— | 4-CF₃-C₆H₄- | | |

EXAMPLES OF PROCESS FOR PREPARATION OF THE COMPOUNDS OF GENERAL FORMULA (I)

EXAMPLE 1

Preparation of pyrrole-2-carboxamides of Formula (I)

Preparation of Starting Materials:

4-(4-Trifluormethylphenoxy)aniline:

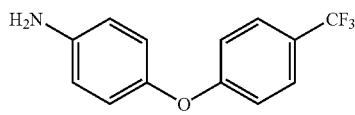

To a stirred solution of 4-trifluormethylbromobenzene (11.2 g, 50 mmol) in dimethylsulphoxide (50 mL) is added powdered potassium carbonate (3.4 g, 60 mmol) and 4-aAminophenol (6.6 g, 55 mmol). The suspension is heated at 90° C. for 4.5 h, then poured into water, extracted with di-isopropylether, filtered, decanted, the organic phase washed with water, dried (magnesium sulphate) and evaporated to give 9.6 g of a brown oil. To this triturated with pentane, the resulting precipitate is filtered, washed with pentane and dried to give 3.3 g of the title compound (27%, mp. 72° C.).

1-Methyl-4-[(allyloxycarbonyl)amino]-3-methoxy-1H-pyrrole-2-carboxylic acid

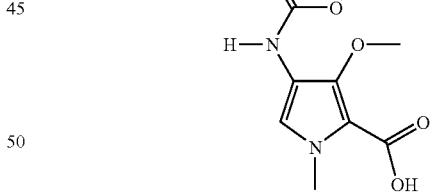

A mixture of 0.93 g (3.3 mmol) of ethyl 1-methyl-4-[(allyloxycarbonyl)amino]-3-methoxy-1H-pyrrole-2-carboxylate (prepared according to the method described in K. Narkunan, M. A. Ciufolini, *Synthesis,* 2000, 673–676), 3.3 ml of a 2 molar sodium hydroxide aqueous solution and 3.3 ml of ethanol is stirred at room temperature for 5 days. Water is added and the ethanol is evaporated. After extraction with diethyl ether, the aqueous phase is acidified to pH 2 with concentrated hydrochloric acid. Extraction with ethyl acetate, drying and concentration give 0.6 g (71% yield) of a light brown solid. (M−1=253).

Coupling Procedure According to Scheme 1:

1-Methyl-4-[(allyloxycarbonyl)amino]-3-methoxy-1H—N-para-[4-(trifluoromethyl)phenoxy]phenyl-pyrrole-2-carboxamide (5)

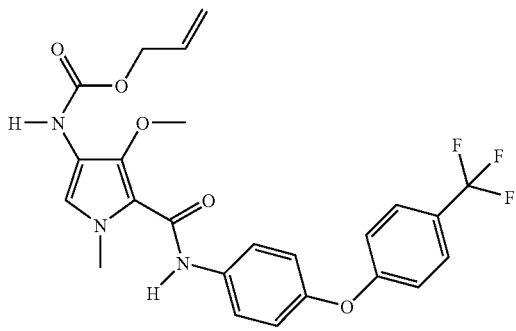

A mixture of 0.127 g (0.5 mmol) of 1-methyl-4-[(allyloxycarbonyl)amino]-3-methoxy-pyrrole-2-carboxylic acid, 0.127 g (0.5 mmol) of 4-[4-(trifluoromethyl) phenoxy]aniline, and 0.105 g (0.55 mmol) of 1-(3-dimethylaminopropyl)-3-ethyl-carbodiimide hydrochloride in 2.5 ml of pyridine is heated at 90° C. for 3 hours. After cooling, the pyridine is evaporated, the resulting dark oil is stirred at 0° C. with 10 ml of a 15% hydrochloric acid solution for 0.5 hour. The resulting precipitate is filtered off and washed with water and with diethyl ether. The solid is chromatographed (ethyl acetate/heptane) to give 0.08 g (33% yield) of a white solid (MP=144° C.).

Functional Group Transformation According to Scheme 1:

1-Methyl-4-amino-3-hydroxy-1H-N-(4-butoxy-phenyl)pyrrole-2-carboxamide (9)

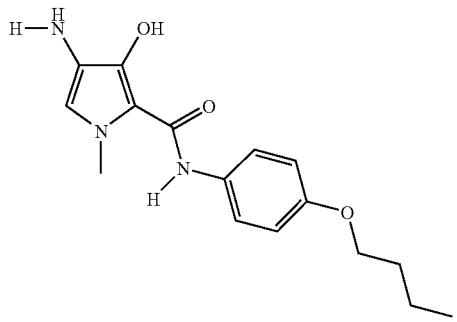

To 0.361 g (0.9 mmol) of 1-Methyl-4-[(allyloxycarbonyl)amino]-3-methoxy-1H-N-(4-butoxy phenyl)-pyrrole-2-carboxamide in 9 ml of dichloromethane at −5° C., 2 ml (2.1 mmol) of a 1 molar solution of boron tribromide in dichloromethane is added drop-wise. The mixture is stirred for 4 hours with the temperature being kept between 0 and 10° C., then for 20 hours at room temperature. The reaction mixture is poured into a mixture of saturated solution of sodium hydrogenocarbonate and ethyl acetate, The precipitate obtained is filtered off and washed with diethyl ether. There is obtained 0.100 g of a solid (M+1=304).

EXAMPLE 2

Preparation of pyrrole-3-carboxamides of Formula (I)

Coupling Procedure According to Scheme 1

1-methyl-2-ethoxycarbonyl-3-hydroxy-1H-N-para-[4-(trifluoromethyl)phenoxy]phenyl-pyrrole-4-carboxamide (15)

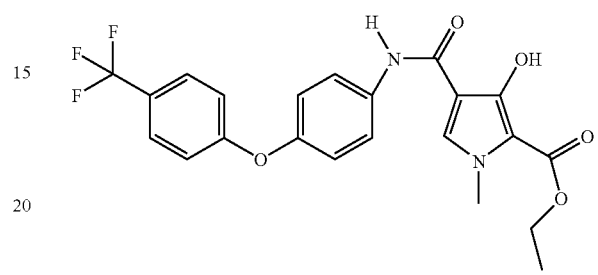

To a mixture of 1.0 g (4.69 mmol) of 1-methyl-2-ethoxycarbonyl-3-hydroxy-1H-pyrrole-4-carboxylic acid (prepared according to the method described in K. Narkunan, M. A. Ciufolini, *Synthesis*, 2000, 673–676), 1.42 g (5.63 mmol) of 4-[4-(trifluoromethyl)phenoxy]aniline, and 0.644 g (4.69 mmol) of 1-hydroxy benzotriazol in 10 ml of tetrahydrofuran cooled to 0° C. is added 1.08 g (5.63 mmol) of 1-(3-dimethylaminopropyl)-3-ethylcarbodiimide hydrochloride in 10 ml of tetrahydrofuran. The resulting mixture is stirred at 0° C. for 2 hours and then heated at 45° C. for 16 hours. After cooling, the tetrahydrofuran is evaporated. The residue is chromatographed (ethyl acetate/heptane 9/1 to 6/4) to give 1.37 g (65% yield) of a yellow solid (M+1=449)

Functional Group Transformation According to Scheme 1:

1-methyl-2-ethoxycarbonyl-3-methoxy-1H-N-para-[4-(trifluoromethyl)phenoxy]phenyl-pyrrole-4-carboxamide (12)

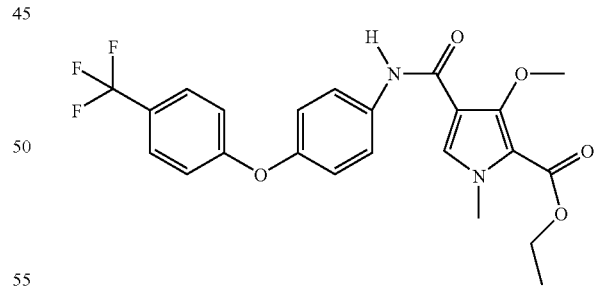

To a mixture of 0.80 g (1.78 mmol) of 1-methyl-2-ethoxycarbonyl-3-hydroxy-1H-N-para-[4-(trifluoromethyl)phenoxy]phenyl-pyrrole-4-carboxamide, 0.49 g (3.57 mmol) of potassium carbonate in 8 ml of acetone under nitrogen, is added 0.20 mL (2.14 mmol) of dimethylsulphate. The resulting mixture is stirred at 50° C. for 16 hours. After concentration, the residue is taken up in water. Extraction with diethyl ether and ethyl acetate, drying, and concentration give 0.745 g (90% yield) of an orange oil (M+1=463)

1-methyl-2-hydroxycarbonyl-3-methoxy-1H-N-para-[4-(trifluoromethyl)phyenoxy]phenyl-pyrrole-4-carboxamide (13)

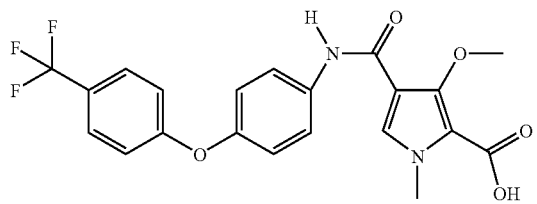

To a solution of 0.64 g (1.39 mmol) of 1-methyl-2-ethoxycarbonyl-3-methoxy-1H-N-para-[4-(trifluoromethyl)phenoxy]phenyl-pyrrole-4-carboxamide in 4 ml of ethanol is added 1.4 ml (2.8 mmol) of a 2 molar sodium hydroxide solution. The resulting solution is stirred at room temperature for 5 days. Water is added and the ethanol is evaporated. After extraction with diethyl ether, the aqueous phase is acidified to pH 2 with concentrated hydrochloric acid. Extraction with ethyl acetate, drying and concentration give 0.5 g (85% yield) of a yellowish solid. (M+1=435).

1-methyl-2-amino-3-methoxy-1H-N-para-[4-(trifluoromethyl)phenoxy]phenyl-pyrrole-4-carboxamide (14)

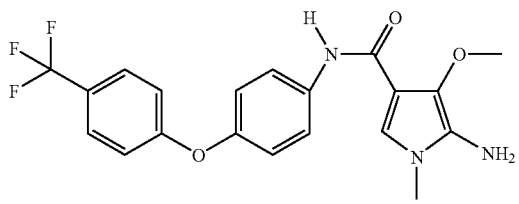

0.46 g (1.05 mmol) of 1-methyl-2-hydroxycarbonyl-3-methoxy-1H-N-para-[4-(trifluoromethyl)phenoxy]phenyl-pyrrole-4-carboxamide is stirred at room temperature for 18 hours in 3.5 ml of thionyl chloride. After concentration, the residue is taken up in di-isopropylether, and the suspension is filtered off. The filtrate is concentrated to give 0.4 g (85% yield) of an orange solid. A solution containing 0.370 g (0.82 mmol) of the obtained acid chloride in 12 ml of acetone is added to a solution of 0.06 g (1 mmol) of sodium azide in 0.2 ml of water. After 0.5 hours of stirring, 12 ml of water is added, and the suspension is filtered off. The solid is washed with water and heptane. The filtrate's phases are separated and the aqueous phase is made basic. Extraction with ethyl acetate, drying and concentration give 0.13 mg (39% yield) of a yellow powder

EXAMPLE 3

Preparation of Pyrazoles of Formula (I)

Coupling Procedure According to Scheme 1:

4-Bromo-1-methyl-5-nitro-N-para-[3-(trifluoromethyl)phenoxy]phenyl pyrazole-3-carboxamide

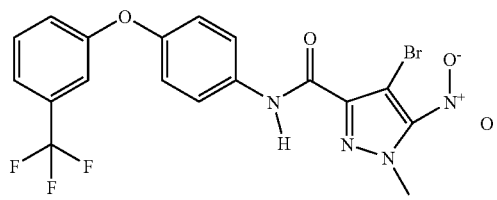

To a mixture of 0.99 g (3.96 mmol) of 1-methyl-4-bromo-5-nitropyrazole-3-carboxylic acid (prepared according to the method described in Y. Manaev, M. Andrea, V. Perevalov, B. Stepanov, V. Dubrovskaya, V. Seraya, *J. Gen. Chem. USSR (Engl. Trans.)* 1982, 2291–2296), 1.00 g (3.96 mmol) of 4-[3-(trifluoromethyl) phenoxy]aniline, and 0.05 g (0.39 mmol) of 1-hydroxybenzotriazole in 50 ml of dichloromethane with ice cooling, is added 0.83 g (4.35 mmol) of 1-(3-dimethylaminopropyl)-3-ethylcarbodiimide hydrochloride in portions. The resulting mixture is stirred at room temperature for 2 hours, and diluted with 150 mL dichloromethane and 100 ml of a 1 molar hydrochloric acid solution. The two phases solution is well shaken, and the phases are separated. The dichloromethylated solution is dried and concentrated to give a yellow solid, which is washed with di-isopropyl ether to give 1.56 g (81% yield) of compound 70 as a solid (M+1=485).

Functional Group Transformation According to Scheme 1:

1-Methyl-4-hydroxy-5-amino-N-para-[3-(trifluoromethyl) phenoxy]phenyl pyrazole-3-carboxamide (44)

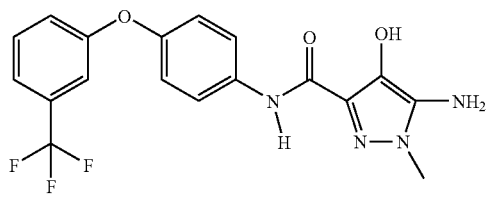

A mixture of 1.5 g (3.1 mmol) of 1-methyl-4-bromo-5-nitro-N-para-[3-(trifluoromethyl)phenoxy]phenyl pyrazole-3-carboxamide, 2.5 g (0.065 mmol) of sodium hydroxide, 25 ml of water, 25 ml of ethanol and 200 mg (0.8 mmol) of copper bromide is stirred at 90° C. for 1 hour, 25 ml of water is added and the mixture is stirred at 100° C. for 3 hours. After cooling, the mixture is diluted with 200 ml of water and made acidic with concentrated hydrochloric acid. After extraction with ethyl acetate, drying and concentration to 5 ml, diethyl ether is added and after 5 minutes of stirring, the resulting solid is filtered off and washed with more diethyl ether to provide 0.54 g of a solid. Of this solid, 0.47 g (1.11 mmol) were mixed with 0.10 g of 5% palladium on charcoal in 50 ml of methanol and stirred at room temperature under hydrogen at 60 psi for 3 hours. Filtration through silica and washing with acetic acid, concentration give a green solid which is washed with diethyl ether to give 0.15 g (34% yield) of 71 as a grey solid (M+1=393).

EXAMPLE 4

Preparation of Isoxazoles of Formula (I)

Preparation of Starting Material:

3-(methoxycarbonyl)amino-4-methoxy-isoxazole-5-carboxylic acid

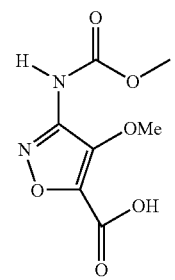

A mixture of 2.50 g (0.011 mmol) of methyl-3-(methoxycarbonyl)amino-4-methoxy-isoxazole-5-carboxylate (prepared according to the method described in W. Kloetzer, J. Schantz, *Monatsh. Chem.*, 1965, 102–115) and 1.30 g of powdered sodium hydroxide dissolved in 9 ml of water is heated at 90° C. for 3 hours. After cooling, the mixture is acidified to pH=2 with concentrated hydrochloric acid, controlling the temperature so as not to exceed 5° C. After 1 hour of stirring at 0° C., the precipitate obtained is filtered off and washed with cold water. There is obtained 2.01 g (86% yield) of a white solid (M+1=217).

Coupling Procedure According to Scheme 1:

3-[(Methoxycarbonyl)amino]-N-para-[4-(trifluoromethyl)phenoxy]phenylisoxazol-5-carboxamide (28)

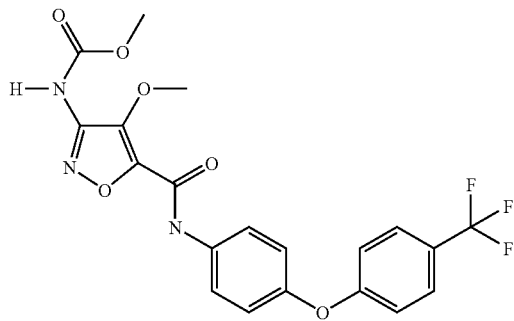

A mixture of 0.162 g (0.75 mmol) of 3-(methoxycarbonyl)amino-4-methoxy-isoxazole-5-carboxylic acid, 0.172 g (0.68 mmol) of 4-[4-(trifluoromethyl)phenoxy]aniline and 0.212 g (0.75 mmol) of 4-(4,6-dimethoxy-1,3,5-triazin-2-yl)-4-methylmorpholinium chloride in 5 ml of ethanol is heated at 70° C. for 6 hours, and then stirred at room temperature for 16 hours. After evaporation of the ethanol, the residue is taken up in ethyl acetate and the resulting solution is washed successively with a saturated solution of sodium hydrogenocarbonate, water, 2% solution of hydrochloric acid, and water. After drying and concentrating, the residue is chromatographed (ethyl acetate/heptane, 2:8) to give 0.122 g (37% yield) of a cream solid (M+1=452).

Functional Group Transformation According to Scheme 1:

3-Amino4-hydroxy-N-para-[4-(trifluoromethyl)phenoxy]phenylisoxazole-5-carboxamide (32)

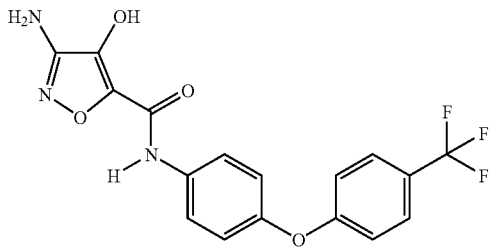

To 0.122 g (0.27 mmol) of 3-[(methoxycarbonyl)amino]-N-para-[4-(trifluoromethyl)phenoxy]phenylisoxazole-5-carboxamide in 2 ml of dichloromethane at 0° C., 0.62 ml (0.62 mmol) of a 1 molar solution of boron tribromide in dichloromethane is added drop-wise. The mixture is stirred for 4 hours with the temperature being kept between 0 and 10° C., then for 20 hours at room temperature. The reaction mixture is poured into a saturated solution of sodium hydrogenocarbonate, and the phases are separated. The aqueous phase is further extracted with ethyl acetate. The combined organic phases are dried and concentrated. The residue is stirred in acetonitrile and the resulting suspension is filtered off to give a cream solid.

EXAMPLE 5

Preparation of Isoxazole-3-carboxamides of Formula (I)

Coupling Procedure According to Scheme 1:

2-methoxycarbonyl-3-methoxy-N-para-[4-(trifluoromethyl)phenoxy]phenylisoxazole-4-carboxamide (39)

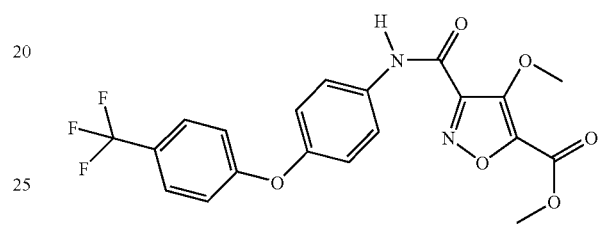

To a suspension of 1 g (4.4 mmol) of 2-azidocarbonyl-3-methoxy-isoxazole-4-carboxylic acid (prepared according to the method described in W. Kloetzer, J. Schantz, *Monatsh. Chem.*, 1965, 102–115) in 10 ml of water cooled at 0° C., is added drop-wise a solution of 3.36 g (13.2 mmol) of 4-[4-(trifluoromethyl)phenoxy]aniline in 15 ml of tetrahydrofuran. The resulting mixture is stirred at 0° C. for 5 hours and left to stand at room temperature for 16 hours. After concentration, the residue is taken up in ethyl acetate and the organic phase is washed successively with a 1% hydrochloric acid solution, and with brine. Drying and concentration give a solid which is purified on silica to give 0.72 g (38% yield) of a white solid (M+1=436).

Functional Group Transformation According to Scheme 1:

2-hydroxycarbonyl-3-hydroxy-N-para-[4-(trifluoromethyl)phenoxy]phenyl-isoxazole-4-carboxamide (40)

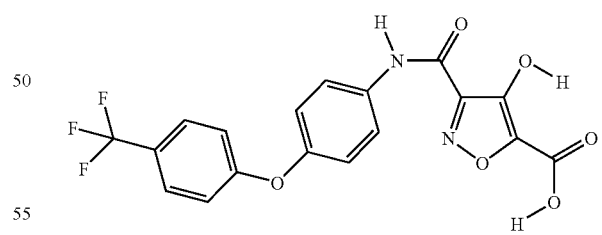

A mixture of 0.64 g (1.47 mmol) of 2-methoxycarbonyl-3-methoxy-N-para-[4-(trifluoromethyl)phenoxl]phenyl-isoxazole-4-carboxamide, 0.98 g (7.4 mmol) of lithium iodide, and 0.12 g (1.47 mmol) of sodium acetate in 5 ml of dimethylformamide is heated at 90° C. for 8 hours, left to stand at room temperature and heated at 90° C. for 6 hours. After cooling, 15 ml of water is added, the solution is made basic with a 30% sodium hydroxide solution and washed 3 times with diethyl ether. The aqueous phase is acidified with a concentrated hydrochloric acid solution. After extraction with ethyl acetate, the organic phase is washed with a saturated lithium chloride solution, dried, and concentrated to give 0.33 g (56% yield) of a solid.

EXAMPLE 6

Preparation of Pyridine-4-carboxamides of Formula (I)

Preparation of Starting Material:

[(2-Diethylamino-oxazole[4,5-b3]pyridine]-4-carboxylic acid

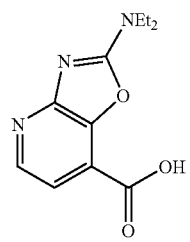

A solution of t-butyl-[(2-diethylamino-oxazolo[4,5-b3] pyridine]-4-carboxylate (0.76 g, 2.61 mmol) was prepared as described in the literature (R. K. Russel et al., *Tetrahedron Lett.* 1993, 34, 203–206) and the crude material refluxed for 3 hours in formic acid (15 mL). Then all volatiles were removed, the residue taken up in trichloromethane out of which the pure material precipitated upon cooling (577 mg, 94%). (M+1=236).

Coupling Procedure and Functional Group Transformation According to Scheme 1:

[4-(Trifluoromethyl)phenoxy]anilino-(2-amino-3-hydroxy) pyridyl-4-carboxamide (19)

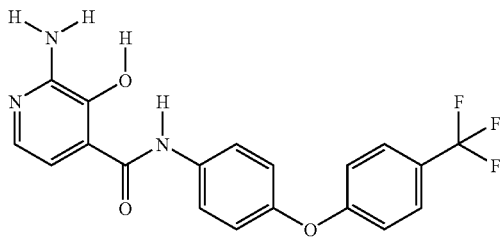

To a mixture of [(2-diethylamino-oxazolo[4,5-b3]pyridine]-4-carboxylic acid (0.30 g, 1.28 mmol), 4-dimethylaminopyridine (16 mg, 0.13 mmol) and 4-(trifluoromethyl) phenoxyl]anilin (0.39 g, 1.53 mmol) in pyridine (15 mL) was added dimethylamino-propylethylcarbodiimide (0.28 g, 1.79 mmol). The reaction mixture was stirred for 3d, then all volatiles removed, the crude taken up in ethylacetate, extracted with pH 4 buffer solution, the organic phase separated, dried (magnesium sulphate), evaporated and the residue purified by chromatography (silica, heptane/ethyl acetate) to give 256 mg of a yellow solid. 100 mg of this solid were dissolved in dimethylsulphoxide (2 mL) to which was added 50% aqueous potassium hydroxide (3 mL), the solution was stirred for 2 h at 80° C., then cooled to room temperature, poured into pH4 buffer solution and extracted with ethyl acetate. After drying the organic phase (magnesium sulphate),evaporation of all volatiles and chromatography, 31 mg of the desired product was obtained as yellow solid (38%). (M–1=388).

EXAMPLE 7

Preparation of Isothiazoles of Formula (I)

Coupling Procedure According to Scheme 1:

5-Nitro-N-para-[4-(trifluoromethyl)phenoxy]phenyl-isothiazole-3-carboxamide (58)

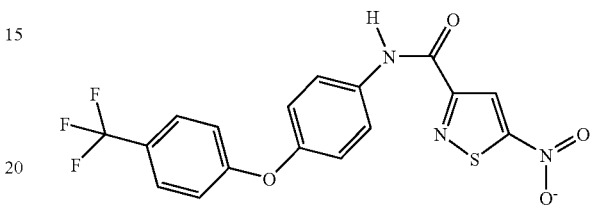

To 0.8 g (4.6 mmol) of 5-nitro-isothiazole-3-carboxylic acid (prepared according to the method described in R. J. A. Walsh, K. R. H. Woolbridge, *J. Chem. Soc. Perkin Trans* 1, 1972, 1247–1249) is added 14 ml of thionyl chloride under nitrogen, and the resulting mixture is stirred at reflux for 3 hours. After cooling, the solvent is evaporated to give a solid. This solid is suspended in a mixture of 20 ml of diethyl ether and 20 ml of dichloromethane. The suspension is added to a mixture of 2.74 g (10.8 mmol) of 4-[4-(trifluoromethyl)phenoxy]aniline and 2.5 ml (18.3 mmol) of triethylamine in 40 ml of diethyl ether. The resulting mixture is stirred at room temperature for 4 hours and left to stand at room temperature overnight. The resulting suspension is filtered, the filtrate is washed with a saturated sodium chloride solution, then dried and concentrated to give a brown solid which is chromatographed (ethyl acetate/heptane) to give 1.2 g (63% yield) of an orange solid (M+1=410).

Functional Group Transformation According to Scheme 1:

5-Amino-N-para-[4-(trifluoromethyl)phenoxy]phenyl-isothiazole-3-carboxamide (42)

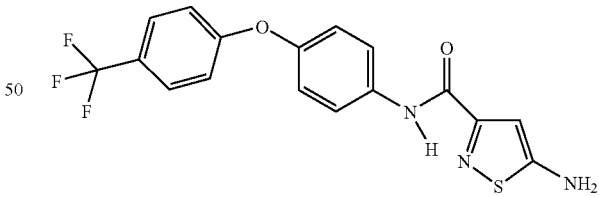

To a solution of 1.05 g (2.57 mmol) of 5-nitro-N-para-[4-(trifluoromethyl)phenoxy]phenyl-isothiazole-3-carboxamide in 5 ml of concentrated hydrochloric acid is added a solution of 2.5 g (12.8 mmol) of tin chloride in 5 ml of concentrated hydrochloric acid and the resulting mixture is heated at 70° C. for 16 hours. After cooling, the solvent is evaporated, and the residue is taken up in water. The aqueous phase is made basic with a 30% sodium hydroxide solution. After extraction with ethyl acetate, drying, and concentration, the residue is chromatographed (ethyl acetate/heptane) to give 0.580 g (60% mmol) of a light brown solid (M+1=380).

EXAMPLE 8

Preparation of Thiophene-2-carboxamides of Formula (I)

Coupling Procedure According to Scheme 1:

4-Bromo-3-methoxy-N-4-[4(trifluoromethyl)phenoxy]phenyl-thiophene-2-carboxamide

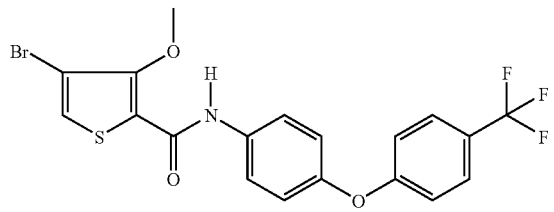

To 2.39 g (10 mmol) of 4-bromo-3-methoxy thiophene-2-carboxylic acid (prepared according to the method of C. Corral, M. B. El-Ashmawy, J. Lissavetzky, A. Basilio, A. Giraldez, *Eur. J. Med. Chem.* 1987, 22, 251–254) was added 10 ml of thionyl chloride, the mixture was refluxed for 2 hours, cooled to room temperature and the excess thionyl chloride removed by evaporation. The crude acid chloride in 10 ml of dry tetrahydrofuran was added drop wise to a stirred mixture of 0.53 g (10 mmol) of 4-(4-trifluorophenoxy)aniline and 1.01 g (10 mmol) of triethylamine in 20 ml of dry tetrahydrofuran at 0° C., the mixture stirred at room temperature for 18 hours, treated with 150 mL of water and extracted with diethyl ether, dried and evaporated to yield a solid, which was washed with pentane to yield 4.43 g (94% yield) of a buff solid (M+1=473).

Functional Group Transformation According to Scheme 1:

2-N-4-[4(Trifluoromethyl)phenoxy]phenylcarboxamide-3-methoxythiophene-4-carboxylic acid (3)

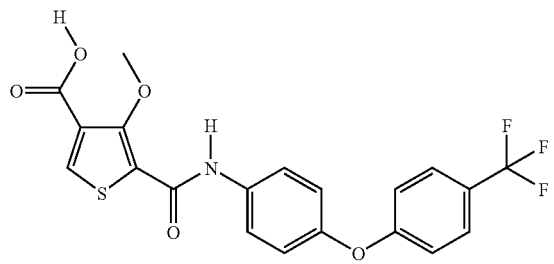

To 2.00 g (4.24 mmol) of 4-bromo-3-methoxy-N-4-[4-(trifluoromethyl) phenoxy]phenyl-thiophene-2-carboxamide in 40 ml of dry tetrahydrofuran at −78° C., was added drop-wise 6 ml (8.9 mmol) of n-butyllithium (1.6M in hexane) the reaction stirred at −78° C. for 1 hour before he mixture was poured onto an excess of dry ice and allowed to warn to room temperature. After treatment with 50 mL of water and extraction with diethyl ether, the aqueous fraction was acidified to pH3 with aqueous hydrogen chloride and extracted with dichloromethane, dried and evaporated to yield a solid, washed with 5% diethyl ether in pentane and filtered to yield 1.11 g (54% yield) of a buff solid (M+1=438).

4-[(Allyloxycarbonyl)amino]-3-methoxy-N-4-[4-(trifluoromethyl)phenoxy]phenyl-thiophene-2-carboxamide (2)

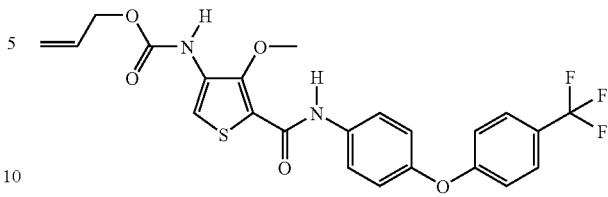

To 0.5 g (1.14 mmol) of 2-N-4-[4(trifluoromethyl)phenoxy]phenyl carboxamide-3-methoxy thiophene-4-carboxylic acid in 5 ml of acetonitrile under argon was added 0.116 g (1.14 mmol) of triethylamine and 0.315 g (1.14 mmol) of diphenylphosphorylazide, the mixture was heated at 85° C. for 2 hours, 2.5 ml of allyl alcohol was added and the heating continued for 18 hours. The mixture was cooled to room temperature and evaporated, the residue was chromatographed (dichloromethane/heptane) to yield 0.15 g (27% yield) of a pale yellow solid (M+1=493).

4-Methylthio-3-methoxy-N-4-[3-(trifluoromethyl)phenoxy]phenyl-thiophene-2-carboxamide (4)

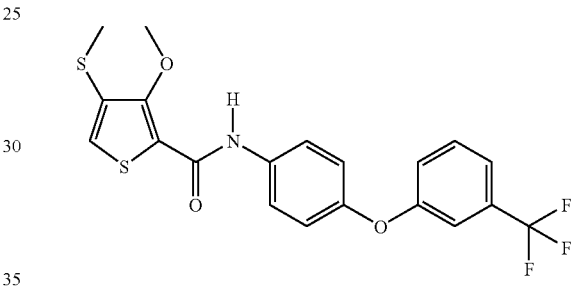

To 0.1 g (0.21 mmol) of 4-bromo-3-methoxy-N4-[3(trifluoromethyl) phenoxy]phenyl-thiophene-2-carboxamide in 2 ml of dry tetrahydrofuran, at −78° C., was added drop-wise 0.3 mL (0.45 mmol) of n-butyl lithium (1.6M in hexane). The mixture was stirred at −78° C. for 1 hour, treated with 0.02 g ((0.21 mmol) of dimethyl disulphide in 0.5 ml of dry tetrahydrofuran, stirred at −78° C. for 3 hours and 18 hours at room temperature. The mixture was poured into 25 ml of water and extracted with dichloromethane, dried and evaporated to yield an oil, chromatographed (dichloromethane/heptane) to yield 0.035 g (38% yield) of a colourless oil (M+1=440).

EXAMPLE 9

Preparation of Nicotinamide of Formula (I)

Preparation of Starting Materials:

3-methyl-4-methoxy pyridine

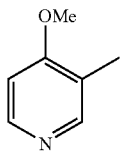

A mixture of 4 g (28.8 mmol) 3-methyl-4-methoxy pyridine N-oxide (prepared according to the method described in Kohl, Bernhard et al; *J. Med. Chem.;* 1992; 1049–1057) and 1.1 mg of 5% palladium on charcoal in 50 ml of methanol is hydrogenated at 20 atms at room temperature for 12 hours (2*6 hours). Filtration through celite, and evaporation gave 3,2 g (90%) of a light green oil.

3-methyl-4-methoxy-5-nitro pyridine

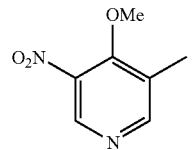

30 ml of 100% nitric acid is added to 150 ml of 98% sulphuric acid with stirring and cooling. To this solution is added dropwise 3.2 g (26 mmol) of 3-methyl-4-methoxy pyridine. The mixture is stirred at 80° C. for 2.5 hours, cooled down and added cautiously to a mixture of 400 g of crushed ice and 300 g of potassium carbonate with external cooling. 125 g more of potassium carbonate is added, and the suspension is filtered. The cake is washed with around 1 l of diethyl ether. The filtrate layers are separated, the ethereal layer is dried, filtered off and concentrated to give 2.9 g (30% yield) of a yellow oil (M+1 =169) (purity #80%, used with no further purification).

5-nitro-4-hydroxy-nicotinic acid

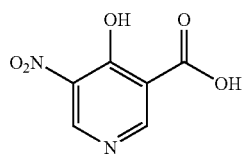

1.5 g (8.9 mmol) of 3-methyl-4-methoxy-5-nitro pyridine is added with stirring to 25 ml of ice cold concentrated sulphuric acid. 3.23 g (11.0 mmol) of potassium dichromate is added in portions over ¾hours, keeping the temperature between 45–55° C. Stirring is continued for ½ hours, and the mixture is poured into 28 g of ice. Ph is adjusted to 1–2 by addition of a 28% aqueous ammonium solution with cooling. The precipitate is filtered off and washed with small amount of very diluted aqueous HCl. After drying, 0.95 g (58% yield) of a white solid (M+1=185) is obtained.

Coupling Procedure According to Scheme 1:

5-nitro-4-hydroxy-N-para-[3-(trifluoromethyl)phenoxy] phenyl nicotinamide

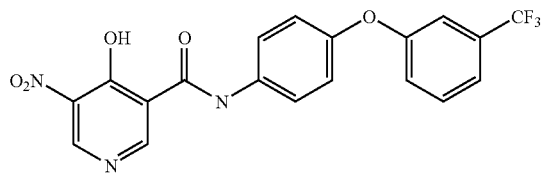

A mixture of 400 mg (2.17 mmol) of 5-nitro-4-hydroxy-nicotinic acid, 2 drops of DMF and 20 ml of thionyl chloride is heated at 70° C. for 3 hrs. Thionyl chloride is removed under vacuum and the residue is dissolved in 15 ml of THF. To this solution is added a solution of 549 mg (2.17 mmol) of para-[3-(trifluoromethyl) phenoxy] aniline and 438 mg (4.34 mmol) of triethylamine in 10 ml of THF. The resulting mixture is stirred for ½ hour at room temperature and added to dilute aqueous HCl. The aqueous phase is extracted with ethyl acetate. The combined organic phases are dried and concentrated. The residue is stirred in a solution of 15 ml of methanol, 20 ml of water and 1 g of sodium hydroxide at 70° C. for 1 hrs and added to dilute aqueous HCl. The aqueous phase is extracted with ethyl acetate. The combined organic phases are dried and concentrated to near dryness. Dilution with ether offered a solid which was filtered off and washed with ether. There is obtained 418 mg (44% yield) of a yellow solid (M−1=418).

Functional Group Transformation According to Scheme 1:

5-amino-4-hydroxy-N-para-[3-(trifluoromethyl)phenoxy] phenyl nicotinamide (45)

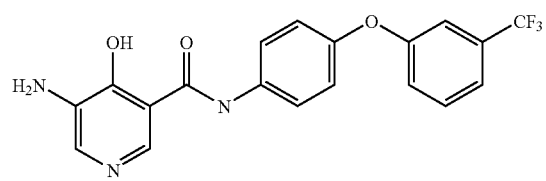

A mixture of 200 mg (0.47 mmol) of 5-nitro-4-hydroxy-N-para-[3-(trifluoromethyl) phenoxy]phenyl nicotinamide and 100 mg of 5% palladium on charcoal in 30 ml of methanol is hydrogenated at 10 atms at room temperature for 2 hours. Filtration through celite, and evaporation gave an oil. Trituration with diisopropylether offered 125 mg (67% yield) of a grey solid (M−1=388)

EXAMPLE 10

Preparation of Nicotinamides of Formula (I)

Preparation of Starting Materials:

2,6-dimethyl-4-hydroxy-nicotinic acid

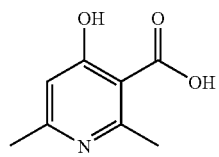

10 g (59.5 mmol) of 2,6-dimethyl-4-oxo-4H-pyran-3-carboxylic acid (prepared according to the method described in Collie, *J. Chem. Soc.;* 1907; 787) is stirred in 100 ml of 28% aqueous ammonia at room temperature overnight. The residue is diluted with little aqueous HCl, and the solid is filtered off. There is obtained 6.9 g (69% yield) of a solid.

2,6-dimethyl-5-nitro-4-hydroxy-nicotinic acid

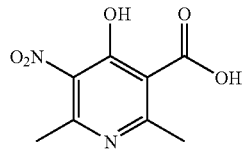

20 ml of 90% nitric acid is added to 100 ml of 98% sulphuric acid with stirring and cooling. To this solution is added portion-wise 6.9 g (41.1 mmol) of 2,6-dimethyl-4-hydroxy-nicotinic acid. The mixture is stirred at 80° C. for 1 hour, cooled down and added cautiously 300 g of crushed ice. The resulting suspension is filtered off. The cake is washed with water and dried. There is obtained 6.7 g (77%) of a white solid.

Coupling Procedure According to Scheme 1:

2,6-dimethyl-5-nitro-4-hydroxy-N-para-(1,1,2,2 tetrafluoroethoxy)phenyl nicotinamide

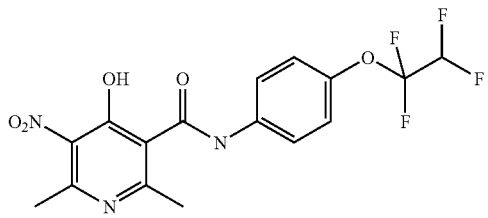

A mixture of 1.0 g (4.7 mmol) of 2,6-dimethyl-5-nitro-4-hydroxy-nicotinic acid in 20 ml of thionyl chloride is heated at 70° C. for 3 hrs. Excess thionyl chloride is removed under vacuum and the residue is suspended in 40 ml of THF. To this is added a solution of 0.99 g (4.7 mmol) of para (1,1,2,2 tetrafluoroethoxy) aniline and 1 ml (7.1 mmol) of triethylamine in 10 ml of THF. The resulting mixture is stirred for ½ hour at room temperature and the THF is removed under vacuum. The residue is partitioned between aqueous HCl and ethyl acetate. The organic phase is dried and filtered through silica. The filtrate is evaporated to give 1.53 g (80% yield) of a pink solid (M+1=404).

Functional Group Transformation According to Scheme 1:

2,6-dimethyl-5-amino-4-hydroxy-N-para-(1,1,2,2 tetrafluoroethoxy)phenyl nicotinamide (53)

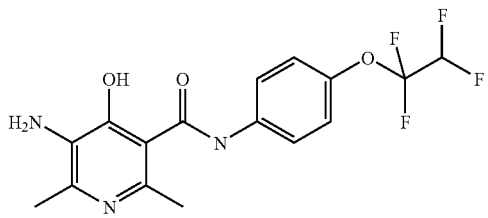

A mixture of 1.4 g (3.47 mmol) of 2,6-dimethyl-5-nitro-4-hydroxy-N-para-(1,1,2,2 tetrafluoroethoxy)phenyl nicotinamide, 1.09 g (17.37 mmol) of ammonium acetate and 0.25 g of 10% palladium on charcoal in 80 ml of methanol is stirred at 70° C. for 3 hours and filtered through celite. Methanol is evaporated and the residue is partitioned between water and ethyl acetate. The phases are separated and the organic layer is dried and evaporated. The residue is washed with diisopropyl ether, filtered off and dried. There is obtained 0.96 g (74% yield) of a yellow solid (M+1=374).

2,6-dimethyl-5-(2,5-dimethyl-pyrrol-1-yl)-4-hydroxy-N-para-(1,1,2,2 tetrafluoroethoxy)phenyl nicotinamide (54)

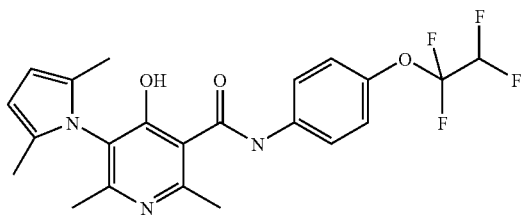

A mixture of 300 mg (0.8 mmol) of 2,6-dimethyl-5-amino-4-hydroxy-N-para-(1,1,2,2 tetrafluoroethoxy)phenyl nicotinamide and 183 mg (1.6 mmol) of acetonylacetone in 5 ml of acetic acid is heated at 70° C. for 15 minutes. The mixture is added to aqueous NaHCO$_3$, and extracted in ethyl acetate. The phases are separated and the organic layer is dried and evaporated. The residue is washed with diisopropyl ether, filtered off and dried. There is obtained 285 mg (79% yield) of a white solid (M+1=452).

2,6-dimethyl-5-pyrrol-1-yl-4-hydroxy-N-para-(1,1,2,2 tetrafluoroethoxy)phenyl nicotinamide (55)

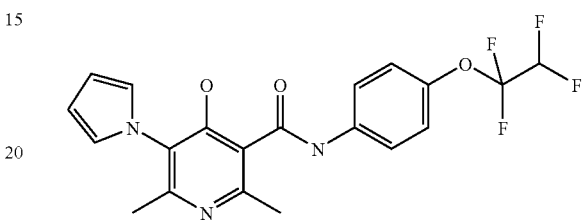

A mixture of 280 mg (0.75 mmol) of 2,6-dimethyl-5-amino-4-hydroxy-N-para-(1,1,2,2 tetrafluoroethoxy)phenyl nicotinamide and 132 mg (1.0 mmol) of 2,5-dimethoxytetrathydrofurane in 6 ml of acetic acid is heated at 70° C. for 1 hour. The mixture is added to aqueous NaHCO$_3$, and extracted in diethyl ether. The phases are separated and the organic layer is dried and filtered through silica. The filtrate is evaporated. The residue is washed with diisopropyl ether, filtered off and dried. There is obtained 137 mg (43% yield) of a white solid (M+1=424).

EXAMPLE 11

Preparation of Nicotinamides of Formula (I)

Preparation of Starting Materials:

Methyl-4-chloro-5-methoxycarbonyl-nicotinate

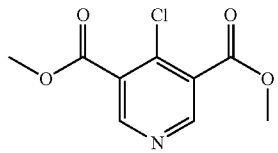

A mixture of 16.38 g (77.6 mmol) of 4-oxo-1,4-dihydropyridine-3,5-dicarboxylic acid dimethyl ester (prepared according to the method described in S. Zupancic, *Heterocycles;* 2000; 2033–2042) and 0.5 ml of DMF in 150 ml of thionyl chloride is heated at reflux for 2 hours. Excess thionyl chloride is removed under vacuum and the residue is added to aqueous NaHCO$_3$, and extracted in ethyl acetate. The phases are separated and the organic layer is dried and evaporated. The residue is washed with aqueous K$_2$CO$_3$ and water, and dried. There is obtained 7.35 g (41% yield) of white solid (M+1=230).

Methyl-4-methoxy-5-methoxycarbonyl-nicotinate

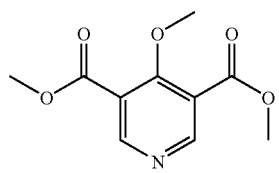

To a solution of 6.3 g (27.5 mmol) of methyl-4-chloro-5-methoxycarbonyl-nicotinate in 100 ml of THF is added 6.48 ml (35 mmol) of a 5.4 m solution of sodium methoxide in methanol. The mixture is stirred for 10 minutes and evaporated. 100 ml of a 0.25M aqueous HCl is added to the residue. The solution is made basic with K₂CO₃ and extracted with ethyl acetate. The organic phase is dried and evaporated to give an oil which crystallised on cooling. There is obtained 6,2 g (quantitative yield) of a solid (M+1=226).

4-methoxy-5-methoxycarbonyl-nicotinic acid

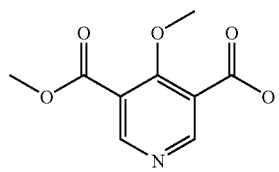

To a solution of 5,3 g (23.5 mmol) of methyl-4-methoxy-5-methoxycarbonyl-nicotinate in 150 ml of methanol and 50 m. of water is added a solution of 0.94 g (23,5 mmol) of sodium hydroxide in 10 ml of water. The resulting mixture is stirred at room temperature overnight. The methanol is removed under vacuum, the aqueous solution is made slightly acidic and extracted with ethyl acetate. The combined organic phases are dried and filtered through silica. The filtrate is evaporated to near dryness and diluted with diisopropyl ether. A precipitate is obtained, filtered off and dried. There is obtained 2,83 g (57% yield) of a white solid (M+1=212).

Coupling Procedure According to Scheme 1:

5-methoxycarbonyl-4-methoxy-N-para-[3-chloro-4-(trifluoromethyl)phenoxy]phenyl nicotinamide (49)

To a mixture of 0.68 g (2.37 mmol) of 4-methoxy-5-methoxycarbonyl-nicotinic acid and 0,50 g (2.37 mmol) of para-[3-chloro-4-(trifluoromethyl)phenoxy] aniline in 25 ml of dichloromethane is added 0.48 g (2.50 mmol) of 1-[3-(N,N-dimethyl-amino) propyl]-3-ethylcarbodiimide hydrochloride in one portion. The solution is stirred at room temperature for 1 hour, and evaporated. The residue is taken up in a mixture of water, ethyl acetate, and 1 ml of 1M aqueous HCl. The organic layer is separated, dried and evaporated. The resulting solid is washed with heptane/diisopropyl ether. There is obtained 0.70 g (61% yield) of a brown solid (M+1=481).

Functional Group Transformation According to Scheme 1:

5-aminocarbonyl-4-methoxy-N-para-[3-chloro-4-(trifluoromethyl)phenoxy]phenyl nicotinamide (50)

A mixture of 0,60 g (1,25 mmol) of 5-methoxycarbonyl-4-methoxy-N-para-[3chloro-4-(trifluoromethyl)phenoxy] phenyl nicotinamide and 10 ml of a 7M solution of ammonia in methanol in 30 ml of methanol is left to stand at room temperature for 3 days. Methanol is evaporated to near dryness (2 ml). The residue is diluted with diethyl ether. The resulting solid is filtered off and dried. There is obtained 0.207 g (35% yield) of a pink solid (M+1=466).

EXAMPLE 12

Preparation of γ-Pyronone-2-carboxamides of Formula (I)

Preparation of Starting Materials:

The starting material 2-Benzyloxy-γ-pyranon-2-carboxylic acid was prepared according to known literature procedures; starting from Furfurylalcohol 2-Hydroxymethyl-pyromeconic acid was synthesized as described by Z. D. Liu, H. H. Khodr. D. Y. Liu, S. L. Lu, R. C. Hider, J. Med. Chem. 1999, 42, 4814–4823. The subsequent benzylation was made as described in Z. D. Liu, S. Piyamongkol, D. Y. Liu, H. H. Khodr, S. L. Lu, R. Hider, Bioorg. Med. Chem. 2001, 9, 563–574. The oxidation of the 3-Benzyloxy-2-hydroxymethyl-γ-pyranon to 2-Benzyloxy-γ-pyranon-2-carboxylic acid was executed as described by J. H. Looker, M. D. Cliffton, J. Heterocycl. Chem. 1986, 23, 225–227

Coupling Procedure According to Scheme 1:

N-(4-Butyloxy-phenyl)-2-(3-benzyloxy-γ-pyranone)-carboxamide

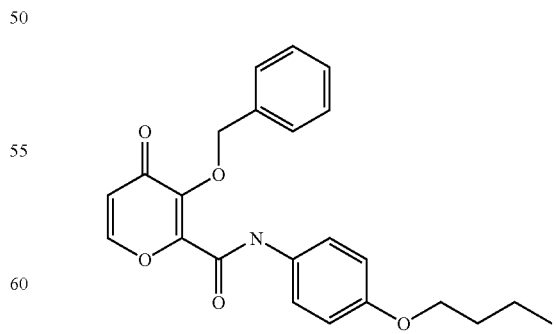

To 2-Benzyloxy-γ-pyranon-2-carboxylic acid (0.5 g, 2 mmol) in dry pyridine (10 mL) was added HOBt (0.27 g, 2 mmol), 4-Butoxyaniline (0.33 g, 2 mmol) and EDCI (0.48 g, 2.5 mmol). The mixture was heated for 1 h at 85° C., then the pyridine evaporated, the residue dissolved and stirred for 15 min in a mixture of CH$_2$Cl$_2$ and 1 M HCl. The layers were separated, the organic portion was washed with H$_2$O, sat. aq. NaHCO$_3$, the emulsion formed filtered, the organic layer separated and dried (MgSO$_4$). After filtration through a pad of SiO$_2$ and subsequent washing with EtOAc, the solvent was evaporated and the residue purified by chromatography (SiO$_2$, pentane/EtOAc 1/1). The product was isolated as an off white solid (311 mg, 0.79 mmol, 39%). Mp. 98–100° C. (M+1=394).

Functional Group Transformation According to Scheme 1:

N-(4-Butyloxy-phenyl)-2-(3-hydroxy-γ-pyranone)-carboxamide (59)

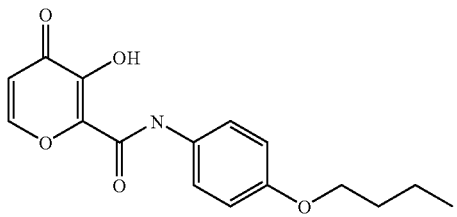

A suspension of N-(4-butyloxy-phenyl)-2-(3-benzyloxy-g-pyranone)-carboxamide (0.26 g, 0.66 mmol) in 4 M HCl (25 mL) and EtOH (15 mL) was heated to 100° C. for 3.5 h. The reaction mixture was cooled down and the suspension formed upon cooling was concentrated in vacuo. The residue was filtered off, washed with H$_2$O and MeOH, to give an off white solid (98 mg, 0.32 mmol, 49%). Mp. 202–204° C.

EXAMPLE 13

Preparation of Pyrrolidin-3-carboxamides of Formula (I)

Preparation of Starting Materials:

The heterocyclic acid was prepared according to T. Högberg, P. Ström, M. Ebner, S. Rämsby J. Org. Chem. 1987, 52, 2033–2036:

Tert. butyl-(1-N-isopropyl-4-hydroxy-5-dioxo-2,5-dihydro-1H)-pyrrol-3-carboxylate

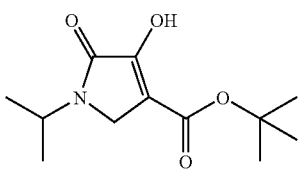

To a solution of i-Propylamine (6.65 mL, 78 mmol) in tert.-butanol (40 mL) under nitrogen was added dropwise tert.-Butylacrylate (11.3 mL, 78 mmol), the mixture was stirred overnight, then diethyloxalate was added (10.6 mL, 78 mmol) at r.t.. Stirring was continued for 2 h, then tert.-BuOK was added (87 mg, 78 mmol) and the mixture refluxed for 2 h, then cooled down and the volatiles removed in vacuo. The crude product was dissolved in hot water, acidified to pH 4. The resulting white precipitate was collected by filtration, dried, to give 10.75 g of product (57%). Mp. 152° C. (M+1=186).

Coupling Procedure According to Scheme 1:

N-4-(phenoxy)phenyl-(1-N-isopropyl-4-hydroxy-5-dioxo-2,5-dihydro-1H)-pyrrol-3-carboxamide (72)

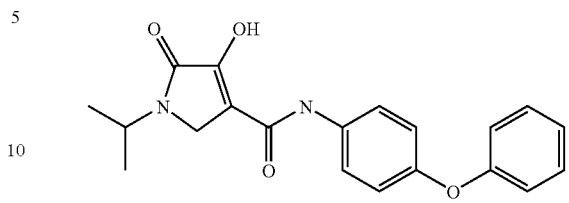

To 0.24 g (1 mmol) of tert.-butyl-(1-isopropyl-4-hydroxy-5-dioxo-2,5-dihydro-1H)-pyrrol-3-carboxylate in dry toluene (5 mL) under N2 was added 4-Phenoxy-anilin (185 mg, 1 mmol) and the mixture was refluxed for 4 h. After cooling to r.t., crystals formed that were collected by filtration to give 70 mg of pure material (0.2 mmol, 20%). Mp. 251° C. (M+1=353).

N-(4-(4-Trifluormethyl)phenoxy)phenyl-[(1-isopropyl-4-hydroxy-5-dioxo-2,5-dihydro-1H)-pyrrol]-3-carboxamide (73)

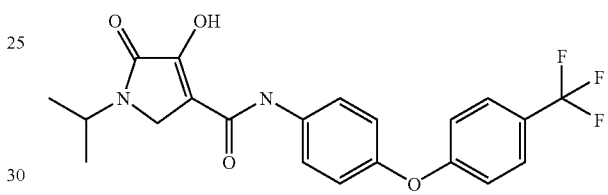

To Ethyl-[(1-isopropyl-4-hydroxy-5-dioxo-2,5-dihydro-1H)-pyrrol]-3-carboxylate (0.2 g, 0.94 mmol), prepared as described by J. B. Campbell, J. W. Firor, J. Org. Chem. 1995, 60(23), 7687–7689, in toluene (5 mL) under N$_2$ was added 4-(4-Trifluormethyl)phenoxy)-anilin (0.3 g, 1.2 mmol). The reaction was refluxed for 2 h, then the solvent evaporated and the residue purified by HPLC-chromatography. The product was obtained as white crystals (83 mg, 21%). (M−1=419)

Examples of Biological Activity of the Compounds of the Invention

EXAMPLE 14

In vivo Test on *Alternaria brassicae* (Leaf Spot of Crucifers)

An aqueous suspension, at a concentration of 1.5%, of the active material tested is obtained by grinding it finely in a formulation of concentrated suspension type. This aqueous suspension is then diluted in water so as to obtain the desired active material concentration. Radish plants (Pernot variety) in starter cups, sown on a 50/50 peat soil-pozzolana substrate and grown at 18–20° C., are treated at the cotyledon stage by spraying with the aqueous suspension described above. Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12–13 day-old culture. The contaminated radish plants are incubated for 6–7 days at about 18° C., under a humid atmosphere. Grading is carried out 6 to 7 days after the contamination, in comparison with the control plants. Under these conditions, good (at least 50%) or total protection is observed at a dose of 500 g/ha with the following compounds: 1, 10, 11, 15, 17, 23, 24, 25, 26, 28, 31, 32, 37, 42, 47, 48, 51, 52, 59, 60, 61, 62, 64, 65, 66, 67, 68, 69, 70, 71, 72.

EXAMPLE 15

In vivo Test on *Septoria nodorum*
(Wheat Glume Blotch)

An aqueous suspension, at a concentration of 1.5%, of the active material tested is obtained by grinding it finely in a formulation of concentrated Suspension type. This aqueous suspension is then diluted in water so as to obtain the desired active material concentration.

Wheat plants (Scipion variety) in starter cups, sown on a 50/50 peat soil-pozzolana substrate and grown at 12° C., are treated at the 1-leaf stage (10 cm tall) by spraying them with the aqueous suspension described above. Plants, used as controls, are treated with an aqueous solution not containing the active material. After 24 hours, the plants are contaminated by spraying with an aqueous suspension of *Septoria nodorum* spores (500,000 spores per cm$^3$). The spores are collected from a seven-day-old culture. The contaminated wheat plants are incubated for 72 hours at about 18° C., under a humid atmosphere, and then for 14 days at 90% relative humidity.

Grading is carried out 15 to 20 days after contamination, in comparison with the control plants. Under these conditions, good (at least 50%) or total protection is observed, at a dose of 500 g/ha, with the following compounds: 10, 16, 17, 19, 28, 32, 33, 39, 43, 46, 49, 52, 53, 63, 64, 65, 66, 67, 68, 72.

EXAMPLE 16

In vivo Test on *Erisyphe graminis* f. sp. *tritici*
(Powdery Mildew of Wheat)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Audace variety) in starter cups, sown on 50/50 peat soil-pozzulana substrate and grown at 12° C., are treated at the 1-leaf stage (10 cm tall) by spraying with the aqueous suspension described above. Plants, used as controls, are treated with an aqueous solution not containing the active material. After 24 hours, the plants are contaminated by dusting them with *Erisyphe graminis* f. sp. *tritici* spores, the dusting being carried out using diseased plants.

Grading is carried out 7 to 14 days after the contamination, in comparison with the control plants. Under these conditions, good (at least 50%) or total protection is observed, at a dose of 500 g/ha, with the following compounds: 5, 11, 12, 13, 14, 15, 19, 22, 24, 25, 26, 27, 28, 29, 30, 31, 32, 34, 35, 36, 37, 42, 44, 45, 49, 51, 55, 59, 64, 65, 66, 67, 68, 69, 70, 71, 73.

Example 17

In vivo Test on *Septoria tritici*
(Leaf Spot of Wheat)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Septoria tritici* spores (500,000 spores per mL). The spores are collected from a 15-day-old culture and are suspended in a nutrient solution composed of:

1.5 g/L of gelatine
0.5 g/L of sodium oleate
24 g/L of PDB

The contaminated wheat plants are incubated for 72 hours at about 20° C. and at 100% relative humidity, and then for 15 days at 80% relative humidity.

Grading is carried out 15 to 20 days after the contamination, in comparison with the control plants. Under these conditions, good (at least 50%) protection is observed, at a dose of 500 g/ha, with the following compounds: 1, 9, 15, 16, 18, 21, 22, 23, 24, 25, 26, 29, 30, 31, 32, 33, 34, 35, 36, 37, 38, 39, 41, 42, 43, 45, 49, 50, 51, 52, 59, 60, 61, 62, 63, 64, 65, 66, 67, 68, 69, 70, 71, 72.

EXAMPLE 18

In vivo Test on *Drechslera teres* 4(Barley Net Blotch)

An aqueous suspension, at a concentration of 1.5%, of the active material. tested is obtained by grinding it finely in a formulation of concentrated suspension type. This aqueous suspension is then diluted in water so as to obtain the desired active material concentration. Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Dreschslera teres* spores (12,000 spores per mL). The spores are collected from a 12-day-old culture. The contaminated wheat plants are incubated for 24 hours at about 20° C. and at 100% relative humidity, and then for 12 days at 80% relative humidity.

Grading is carried out 12 days after the contamination, in comparison with the control plants. Under these conditions, good (at least 50%) protection is observed, at a dose of 500 g/ha, with the compounds described as example: 9, 13, 14, 15, 18, 20, 21, 22, 24, 26, 27, 30, 31, 32, 33, 34, 35, 36, 37, 41, 43, 45, 47, 49, 62, 69, 70, 72.

EXAMPLE 19

In vivo Test on *Rhynchosporium secalis*
(Barley Leaf Scald)

An aqueous suspension, at a concentration of 1.5%, of the active material tested is obtained by grinding it finely in a formulation of concentrated suspension type. This aqueous suspension is then diluted in water so as to obtain the desired active material concentration. Barley plants (Express or Barrack variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Rhynchosporium secalis* spores (800,000 spores per mL). The contaminated wheat plants are incubated for 48 hours at about 20° C. and at 100% relative humidity, and then for 12/14 days at 80% relative humidity.

Grading is carried out 12/14 days after the contamination, in comparison with the control plants. Under these conditions, good (at least 50%) protection is observed, at a dose of 500 g/ha, with the following compound described as example: 32.

EXAMPLE 20

In vivo Test on *Puccinia recondita* (Wheat Brown Rust)

An aqueous suspension, at a concentration of 1.5%, of the active material tested is obtained by grinding it finely in a formulation of concentrated suspension type, This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Puccinia recondita* spores (150,000 spores per mL). The contaminated wheat plants are incubated for 24 hours at about 20° C. and at 100% relative humidity, and then for 10 days at 70% relative humidity.

Grading is carried out 10 days after the contamination, in comparison with the control plants. Under these conditions, good (at least 50%) protection is observed, at a dose of 500 g/ha, with the following compounds described as example: 6, 10, 11, 12, 13, 14, 15, 28, 29, 30, 31, 34, 37, 42, 45, 46, 50, 51, 52, 62, 72.

EXAMPLE 21

In Vivo Test on *Botrytis cinerea* (Cucumber Grey Mould)

An aqueous suspension, at a concentration of 1.5%, of the active material tested is obtained by grinding it finely in a formulation of concentrated suspension type. This aqueous suspension is then diluted in water so as to obtain the desired active material concentration. Cucumber plants (Marketer variety) in starter cups, sown on a 50/50 peat soil-pozzolana substrate and grown at 18–20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:
20 g/L of gelatine
50 g/L of cane sugar
2 g/L of NH4NO3
1 g/L of KH2PO4

The contaminated cucumber plants are settled for 5/7 days in a climatic room at 15–11° c. (day/night) and at 80% relative humidity.

Grading is carried out 5/7 days after the contamination, in comparison with the control plants. Under these conditions, good (at least 50%) protection is observed, at a dose of 500 g/ha, with the following compounds described as example 5, 24, 30, 37, 45, 67, 69, 70.

What is claimed is:

1. A compound of the formula:

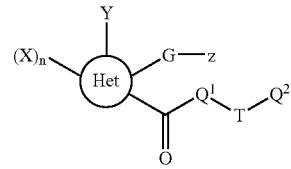

wherein
Het is an isoxazole ring;
X is selected from the group consisting of hydrogen, halogen, —$R^1$ and —$SR^1$;
Y is selected from the group consisting of —NH—(CO)—$R^2$ and —($SO_2$)—$R^1$;
G is selected from the group consisting of —($CH_2$)$_k$—, —O—, —O—(C=O)— and —O—(C=O)—O—;
z is selected from the group consisting of hydrogen, —$R^1$ and halogen;
$Q^1$ is selected from the group consisting of

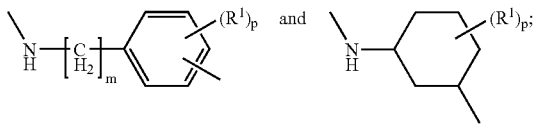

T is selected from the group consisting of —O—, —($CH_2$)$_q$— and —S—;
$Q^2$ is:

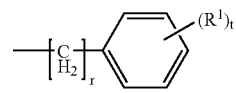

k, m, n, p, q, r and t are independently chosen as being 0, 1, 2, or 3;
$R^1$ is $C_1$–$C_4$ alkyl or $C_1$–$C_4$ alkoxyalkyl;
$R^2$ is oxy-($C_1$–$C_4$)alkylene or oxy-($C_1$–$C_4$)alkyl;
$R^3$ is —OH, —$OR^1$ or —$NH_2$; and
$R^4$ is halogen, alkyl or halogenoalkyl;
as well as N-oxides, geometrical and/or optical isomers, enantiomers and/or diastereoisomers, tautomeric forms, salts and metal and metalloid complexes thereof.

2. The compound of claim 1 wherein
n is 0;
$R^1$ is $C_1$–$C_4$ alkyl;
G is —O—;
z is H;
p and t are independently chosen as being 0, 1 or 2;
$Q^1$ is selected from the group consisting of

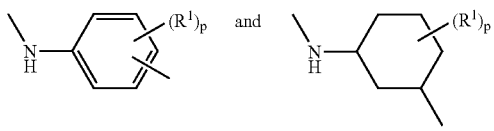

T is —O—; and
Q² is

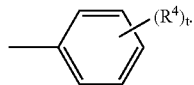

3. Fungicidal composition comprising an effective amount of a compound according to claim 1 and an agriculturally acceptable support.

4. Fungicidal composition according to claim 3, further comprising a surfactant.

5. Fungicidal composition according to claim 3, comprising from 0.05% to 99% by weight of active material.

6. Method for combating the phytopathogenic fungi of crops, characterised in that an effective and non-phytotoxic amount of a composition according to claim 3 is applied to the plant seeds or to the plant leaves and/or to the fruits of the plants or to the soil in which the plants are growing or in which it is desired to grow them.

7. Method according to claim 6, in which the dose of active material applied is between 10 g and 800 g of active material per hectare, in the case of foliar treatments.

8. Method according to claim 6, in which the dose of active material applied is between 50 g and 300 g of active material per hectare in the case of foliar treatments.

9. Method according to claim 6, in which the dose of active material applied is between 2 and 200 g of active material per 100 kg of seed, in the case of seed treatments.

10. Method according to claim 9, in which the dose of active material applied is between 3 g and 150 g per 100 kg of seed, in the case of seed treatments.

11. Fungicidal composition according to claim 4, comprising from 0.05% to 99% by weight of active material.

12. Method for combating the phytopathogenic fungi of crops, characterised in that an effective and non-phytotoxic amount of a composition according to claim 4 is applied to the plant seeds or to the plant leaves and/or to the fruits of the plants or to the soil in which the plants are growing or in which it is desired to grow them.

13. Method for combating the phytopathogenic fungi of crops, characterised in that an effective and non-phytotoxic amount of a composition according to claim 5 is applied to the plant seeds or to the plant leaves and/or to the fruits of the plants or to the soil in which the plants are growing or in which it is desired to grow them.

* * * * *

UNITED STATES PATENT AND TRADEMARK OFFICE
CERTIFICATE OF CORRECTION

PATENT NO. : 7,084,163 B2
APPLICATION NO. : 10/483518
DATED : August 1, 2006
INVENTOR(S) : Stephanie Gary et al.

It is certified that error appears in the above-identified patent and that said Letters Patent is hereby corrected as shown below:

Title Page; should read;
(75) Inventors:  Stéphanie GARY, Lyon (FR); Tim LANGE, Wiesbaden, (DE); Benoît MULLER, Paris (FR); Christopher Richard STEELE, Lyon (FR); Geoffrey Gower BRIGGs, Hertforshire (GB); Joseph PEREZ, Lyon (FR); Alain VILLIER, Saint-Didier-au-Mont-d'OR (FR); Brian HILL, Lyon (FR)

Signed and Sealed this

Eighteenth Day of September, 2007

JON W. DUDAS
*Director of the United States Patent and Trademark Office*